United States Patent
Nicewicz et al.

(10) Patent No.: US 10,017,441 B2
(45) Date of Patent: Jul. 10, 2018

(54) DIRECT ANTI-MARKOVNIKOV ADDITION OF ACIDS TO ALKENES

(71) Applicant: The University of North Carolina at Chapel Hill, Chapel Hill, NC (US)

(72) Inventors: David A. Nicewicz, Durham, NC (US); David S. Hamilton, Carrboro, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 173 days.

(21) Appl. No.: 14/787,179

(22) PCT Filed: May 2, 2014

(86) PCT No.: PCT/US2014/036495
§ 371 (c)(1),
(2) Date: Oct. 26, 2015

(87) PCT Pub. No.: WO2014/179648
PCT Pub. Date: Nov. 6, 2014

(65) Prior Publication Data
US 2016/0096791 A1    Apr. 7, 2016

Related U.S. Application Data

(60) Provisional application No. 61/818,600, filed on May 2, 2013.

(51) Int. Cl.
| | | |
|---|---|---|
| C07C 41/05 | (2006.01) | |
| B01J 31/02 | (2006.01) | |
| C07D 213/89 | (2006.01) | |
| C08F 2/00 | (2006.01) | |
| B01J 31/18 | (2006.01) | |
| B01J 31/22 | (2006.01) | |
| C07D 207/46 | (2006.01) | |
| C07D 209/26 | (2006.01) | |
| C07D 291/06 | (2006.01) | |
| B01J 35/00 | (2006.01) | |
| C07B 37/02 | (2006.01) | |
| C07C 67/00 | (2006.01) | |
| C07D 325/00 | (2006.01) | |
| C08F 4/00 | (2006.01) | |

(52) U.S. Cl.
CPC ........... *C07C 41/05* (2013.01); *B01J 31/0217* (2013.01); *B01J 31/0239* (2013.01); *B01J 31/0244* (2013.01); *B01J 31/1815* (2013.01); *B01J 31/2295* (2013.01); *B01J 35/004* (2013.01); *C07B 37/02* (2013.01); *C07C 67/00* (2013.01); *C07D 207/46* (2013.01); *C07D 209/26* (2013.01); *C07D 213/89* (2013.01); *C07D 291/06* (2013.01); *C07D 325/00* (2013.01); *C08F 2/00* (2013.01); *C08F 4/00* (2013.01); *B01J 2231/324* (2013.01); *B01J 2531/842* (2013.01)

(58) Field of Classification Search
CPC . C07C 41/25; C07C 67/00; C08F 4/00; C08F 2/00; B01J 31/0217; B01J 35/004; B01J 31/2295; B01J 31/0239; B01J 31/1815; B01J 31/0244; B01J 2531/842; B01J 2231/324; C07B 37/02; C07D 325/00; C07D 203/26; C07D 207/46; C07D 213/89; C07D 291/06
See application file for complete search history.

(56) References Cited

U.S. PATENT DOCUMENTS

| | | |
|---|---|---|
| 2006/0224026 A1 | 10/2006 | Schinski et al. |
| 2008/0021071 A1 | 1/2008 | Gravestock et al. |
| 2012/0172634 A1 | 7/2012 | Dong et al. |

FOREIGN PATENT DOCUMENTS

| | | |
|---|---|---|
| WO | WO 2005/077885 A1 | 8/2005 |

OTHER PUBLICATIONS

Chou et al. "Radical-Transfer Hydroamination of Olefins with N-Aminated Dihydropyridines" Chem. Asian J. 2011, 6, 1197-1209.*
International Search Report and Written Opinion, PCT/US2014/036495, dated Mar. 7, 2016.
Bruneau C and Dixneuf PH. Metal vinylidenes in catalysis. Accounts of Chemical Research. 1999; 32(4): 311-323.
Beller M et al. Catalytic Markovnikov and anti-Markovnikov functionalization of alkenes and alkynes: recent developments and trends. Angew. Chem. Int. Ed. 2004; 43(26): 3368-3398.

* cited by examiner

*Primary Examiner* — Mark Eashoo
*Assistant Examiner* — Jessica M Roswell
(74) *Attorney, Agent, or Firm* — Myers Bigel, P.A.

(57) ABSTRACT

A method of making an anti-Markovnikov addition product, comprises reacting an acid with an alkene or alkyne in a dual catalyst reaction system to the exclusion of oxygen to produce said anti-Markovnikov addition product; the dual catalyst reaction system comprising a single electron oxidation catalyst in combination with a hydrogen atom donor catalyst. Dual catalyst composition useful for carrying out such methods are also described.

13 Claims, No Drawings

US 10,017,441 B2

DIRECT ANTI-MARKOVNIKOV ADDITION OF ACIDS TO ALKENES

RELATED APPLICATIONS

This application is a 35 U.S.C. § 371 national phase entry of PCT Application PCT/US2014/036495, filed May 2, 2014, and published in English on Nov. 6, 2014, as International Publication No. WO 2014/179648, and which claims the benefit of U.S. Provisional Application Ser. No. 61/818,600, filed May 2, 2013, the disclosure of each of which is incorporated herein by reference in its entirety.

This invention was made with Government support under grant no. 1-RO1-GM098340-01 awarded by the National Institutes of Health. The US Government has certain rights to this invention.

FIELD OF THE INVENTION

The present invention concerns methods and catalyst systems useful for carrying out addition reactions, particularly anti-Markovnikov additions of acids to alkenes and alkynes.

BACKGROUND OF THE INVENTION

Alkenes are one of the most abundant fine chemical feedstocks, readily accessible from both petrochemical and agrochemical sources. Due to their availability, a multitude of methods have evolved for converting alkenes into the fine chemicals that provide modern society with medicines, agrochemicals, materials and plastics (B. Trost and I. Fleming, Comprehensive Organic Synthesis (1991). One of the most important synthetic reactions of alkenes is with acids, comprising a cornerstone of reactivity in organic synthesis. Moreover, this reaction is integral to the catalysis of important processes such as cationic olefin polymerization (G. Odian, in Principles of Polymerization, 372-463 (2004)) and the addition of nucleophiles to alkenes (Trost and Fleming, supra; M. Beller et al., Angew. Chem. Int. Ed. 43, 3368 (2004)). The regioselectivity of these addition reactions is dictated by a chemical principle, known as Markovnikov's rule, whereby acids add across nucleophilic carbon double bonds to give a preferred site selectivity (M. B. Smith, J. March, March's Advanced Organic Chemistry (2001)). Generally, the alkene and acid polarities align to give the chemical branching depicted in FIG. 1, precluding the direct formation of the opposite, or anti-Markovnikov, isomeric adducts. This has limited the types of chemical structures that can be directly forged via this fundamental organic transformation.

To reverse Markovnikov regioselection is no trivial task and has been cited as one of the preeminent challenges for catalysis in the new century (J. Haggin, Chem. Eng. News 71, 23 (1993)). After decades of effort, the most viable methods are indirect (e.g. alkene hydroboration and oxidative functionalization) and are designed to circumvent the strong bias against the anti-Markovnikov products. Recent disclosures of transition metalcatalyzed direct anti-Markovnikov addition reactions have made strides to reverse this trend but are limited in scope with respect to both acid and alkene (M. Beller et al., supra; G. Dong et al., Science 333, 1609 (2011), M. Utsunomiya et al, J. Am. Chem. Soc. 125, 5608 (2003)). The development of a general and straightforward catalytic strategy to access anti-Markovnikov site selectivity has remained to be identified.

SUMMARY OF THE INVENTION

A first aspect of the invention is a method of making an anti-Markovnikov addition product, comprising: reacting an acid with an alkene or alkyne in a dual catalyst reaction system to the exclusion of oxygen to produce said anti-Markovnikov addition product; the dual catalyst reaction system comprising a single electron oxidation catalyst in combination with a hydrogen atom donor catalyst. The anti-Markovnikov addition product is produced regioselectively in a ratio (weight or molar) of at least 5:1 (or in some embodiments at least 10:1, 20:1, 50:1 or 100:1) of anti-Markovnikov addition product as compared to the corresponding Markovnikov addition product.

A second aspect of the invention is a dual catalyst composition for making an anti-Markovnikov addition product by reacting an acid with an alkene, said dual catalyst composition comprising, consisting of or consisting essentially of a single electron oxidation catalyst in combination with a hydrogen atom donor catalyst, and typically a solvent.

The present invention is explained in greater detail in the drawings herein and the specification set forth below. The disclosures of all US Patent references cited herein are to be incorporated herein by reference.

DETAILED DESCRIPTION OF THE PREFERRED EMBODIMENTS

1. Definitions.

"Addition reaction" as used herein includes both intermolecular addition reactions and intramolecular (e.g., ring-forming) addition reactions.

"Acid" as used herein with reference to reactants in reactions of the present invention may be any suitable acid, typically a Brønsted-Lowry acid, including but not limited to inorganic acids, carboxylic acids, alcohols, amines, thiols, water, malonates, etc.

"Electron withdrawing" group or substituent as used herein describes an atom or group thereof that acts to draw electrons away from another group or substituent. Examples of suitable electron withdrawing substituents include, but are not limited to, halogens (F, Cl, Br, I), nitriles (CN), carboxylic acids (COOH), carbonyls (CO), nitro, aryl (unsubstituted or substituted with electron withdrawing groups), amide (further substituted with alkyl, electron withdrawing groups), sulfonyl (further substituted with alkyl, aryl, electron withdrawing groups), etc.

"Alkyl" as used herein alone or as part of another group, refers to a straight, branched chain, or cyclic, saturated or unsaturated, hydrocarbon containing from 1 or 2 to 10 or 20 carbon atoms, or more. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Lower alkyl" as used herein, is a subset of alkyl, in some embodiments preferred, and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like. The term "akyl" or "loweralkyl" is intended to include both substituted and unsubstituted alkyl or loweralkyl unless otherwise indicated and these groups may be substituted with groups selected from halo (e.g., haloalkyl), alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, aryloxy, ester, amide, sulfonamide, urea, alkoxyacylamino, aminoacyloxy, nitro or cyano where m=0, 1, 2 or 3. Alkyl may be saturated or unsaturated and hence the term "alkyl" as used herein is inclusive of alkenyl and alkynyl when the alkyl substituent contains one or more unsaturated bond (for example, one or two double or triple bonds). The alkyl group may optionally contain one or more heteroatoms (e.g., one, two, or three or more heteroatoms independently selected from O, S, and NR', where R' is any suitable substituent such as described immediately above for alkyl substituents), to form a linear heteroalkyl or heterocyclic group as specifically described below.

"Alkenyl" as used herein refers to an alkyl group as described above containing at least one double bond between two carbon atoms therein.

"Alkynyl" as used herein refers to an alkyl group as described above containing at least one triple bond between two carbon atoms therein.

"Alkylene" as used herein refers to an alkyl group as described above, with one terminal hydrogen removed to form a bivalent substituent.

"Heterocyclic group" or "heterocyclo" as used herein alone or as part of another group, refers to an aliphatic (e.g., fully or partially saturated heterocyclo) or aromatic (e.g., heteroaryl) monocyclic- or a bicyclic-ring system. Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings include quaternized derivatives thereof and may be optionally substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Aryl" as used herein alone or as part of another group, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like. The term "aryl" is intended to include both substituted and unsubstituted aryl unless otherwise indicated and these groups may be substituted with the same groups as set forth in connection with alkyl and loweralkyl above.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Heteroaryl" as used herein is as described in connection with heterocyclo above.

"Alkoxy" as used herein alone or as part of another group, refers to an alkyl or loweralkyl group, as defined herein (and thus including substituted versions such as polyalkoxy), appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like.

"Halo" as used herein refers to any suitable halogen, including —F, —Cl, —Br, and —I.

"Acyl" as used herein alone or as part of another group refers to a —C(O)R radical, where R is any suitable substituent such as aryl, alkyl, alkenyl, alkynyl, cycloalkyl or other suitable substituent as described herein.

"Alkylthio" as used herein alone or as part of another group, refers to an alkyl group, as defined herein, appended to the parent molecular moiety through a thio moiety, as defined herein. Representative examples of alkylthio include, but are not limited, methylthio, ethylthio, tert-butylthio, hexylthio, and the like.

"Alkylamino" as used herein alone or as part of another group means the radical —NHR, where R is an alkyl group.

"Arylalkylamino" as used herein alone or as part of another group means the radical —NHR, where R is an arylalkyl group.

"Disubstituted-amino" as used herein alone or as part of another group means the radical —NR$_a$R$_b$, where R$_a$ and R$_b$ are independently selected from the groups alkyl, haloalkyl, alkenyl, alkynyl, cycloalkyl, cycloalkylalkyl, aryl, arylalkyl, heterocyclo, heterocycloalkyl.

"Acylamino" as used herein alone or as part of another group means the radical —NR$_a$R$_b$, where R$_a$ is an acyl group as defined herein and R$_b$ is selected from the groups hydrogen, alkyl, haloalkyl, alkenyl, alkynyl, cycloalkyl, cycloalkylalkyl, aryl, arylalkyl, heterocyclo, heterocycloalkyl.

"Acyloxy" as used herein alone or as part of another group means the radical —OR, where R is an acyl group as defined herein.

"Ester" as used herein alone or as part of another group refers to a —C(O)OR radical, where R is any suitable substituent such as alkyl, cycloalkyl, alkenyl, alkynyl or aryl.

"Amide" as used herein alone or as part of another group refers to a —C(O)NR$_a$R$_b$ radical or a —N(R$_a$)C(O)R$_b$ radical, where R$_a$ and R$_b$ are any suitable substituent such as alkyl, cycloalkyl, alkenyl, alkynyl or aryl.

"Sulfonyl" as used herein refers to a compound of the formula —S(O)R, where R is any suitable substituent such as alkyl, cycloalkyl, alkenyl, alkynyl or aryl.

"Sulfonyl" as used herein refers to a compound of the formula —S(O)(O)R, where R is any suitable substituent such as alkyl, cycloalkyl, alkenyl, alkynyl or aryl.

"Sulfonate" as used herein refers to a compound of the formula —S(O)(O)OR, where R is any suitable substituent such as alkyl, cycloalkyl, alkenyl, alkynyl or aryl.

"Sulfonic acid" as used herein refers to a compound of the formula —S(O)(O)OH.

"Sulfonamide" as used herein alone or as part of another group refers to a —S(O)$_2$NR$_a$R$_b$ radical, where R$_a$ and R$_b$ are any suitable substituent such as H, alkyl, cycloalkyl, alkenyl, alkynyl or aryl.

"Urea" as used herein alone or as part of another group refers to an —N(R$_c$)C(O)NR$_a$R$_b$ radical, where R$_a$, R$_b$ and R$_c$ are any suitable substituent such as H, alkyl, cycloalkyl, alkenyl, alkynyl or aryl.

"Alkoxyacylamino" as used herein alone or as part of another group refers to an —N(R$_a$)C(O)OR$_b$ radical, where R$_a$, R$_b$ are any suitable substituent such as H, alkyl, cycloalkyl, alkenyl, alkynyl or aryl.

"Aminoacyloxy" as used herein alone or as part of another group refers to an —OC(O)NR$_a$R$_b$ radical, where R$_a$ and R$_b$ are any suitable substituent such as H, alkyl, cycloalkyl, alkenyl, alkynyl or aryl.

2. Acids.

Acids used to carry out the invention may be compounds of the Formula H-X, where X is an organic or inorganic group. Suitable examples of inorganic acids that may be used to carry out the present invention include, but are not limited to, HF, HI, HCl, perchloric acid, nitric acid, sulfuric acid, etc. Suitable examples of organic acids include compounds of the formulas: ROH; RSH; RCOOH; R$_2$NH; and ROC(O)CH$_2$C(O)OR; where each R is an independently selected organic substituent, such as alkyl, alkenyl, alkynl, cycloalkyl, cycloalkenyl, cycloalkynyl, aryl, or covalently coupled combinations thereof such as arylalkyl, alkylaryl, etc. Each may be substituted or unsubstituted, and may optionally contain heteroatoms. In embodiments where the reaction is used to polymerize one or more monomers, at least one of the R groups is alkenyl (optionally substituted) as described further below.

3. Alkenes and Alkynes.

Any suitable alkene (or olefin) or alkyne can be used to carry out the present invention. In some embodiments the alkenes or alkynes may be of the formulas:

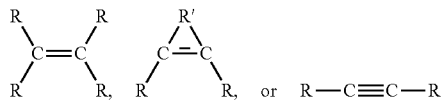

Where each R is independently any suitable substituent such as alkyl, aryl, arylalkyl, alkylaryl, etc., and R' is alkylene (including substituted and unsubstituted embodiments thereof, and optionally heteroatom-containing embodiments thereof, as described above). In some embodiments, such as where the reaction is used to polymerize monomers, the alkene is also an acid. Particular examples of suitable alkenes include but are not limited to those described below.

4. Single Electron Oxidation Catalysts.

Any suitable single electron oxidation catalyst can be used to carry out the present invention, including ground state oxidation catalysts and photocatalysts.

Examples of suitable ground state oxidation catalysts include, but are not limited to, eerie ammonium nitrate, ferrocenium tetrafluoroborate, nitrosyl tetrafluoroborate, iron trichloride, iron (III) tris(phenanthroline)tris(hexafluorophosphate), tris(4-bromophenyl)aminium hexafluoroantimonate, etc.

In some embodiments, the single electron oxidation catalyst is a photocatalyst. Such photocatalysts are known and described in, for example, U.S. Pat. No. 4,937,292 and US Patent Application Publication No. 20070215455 (the disclosures of which are incorporated herein by reference in their entirety). In some embodiments, such photocatalysts have a reduction potential of −1.0 V to +0.1 V against a saturated calomel electrode in 100 percent acetonitrile (as determined by cyclic voltammetry) and have the earliest onset of their emission between 350 and 650 nm. (that is, an excited state reduction potential between +0.5 V to +3.6 V vs. SCE in acetonitrile). Example photocatalysts include, but are not limited to, phenazine, eosin, thiobenzophenone, 9,10-dichloroanthracene, 3,4-benzopyrene, perylene, trans-1,3,5-hexatriene, 1-chloroanthracene, 1,5-dichloroanthracene, 1,10-dichloroanthracene, 1,5,10-trichloroanthracene, 1,4,5,8-tetrachloroanthracene, 9,10-dibromoanthracene, 9-methylanthracene, 9-nitroanthracene, 1-azaanthracene, 2-azaanthracene, acridine, diphenylbutadiene, 3,4,8,9-dibenzopyrene, 7,12-dimethylbenzanthracene, 1,12-benzoperylene trans-1,2-benzanthracene, 9,10-dicyanoanthracene 1,4-dicyanobenzene and 2,4,6-triphenyloxopyrylium tetrafluoroborate.

In some embodiments, the photocatalysts are carbocyclic or heterocyclic aromatic compounds, for example heterocyclic aromatic compounds containing ring nitrogen heteroatoms.

In some embodiments, the photocatalysts are compounds having an anthracene, aza-anthracene or polyaza-anthracene nucleus which is unsubstituted, substituted or polysubstituted at any positions with halogens, except iodine, and/or with one or more lower alkyl or cycloalkyl radicals, and/or with other phenyl substituents.

5. Hydrogen Atom Donor Catalysts.

Suitable hydrogen atom donor catalysts for use in carrying out the present invention are, in general, compounds of formula A-SH (i.e., thiol compounds) where A is alkyl, aryl, or an electron withdrawing group.

6. Catalyst Systems and Methods.

Reactions of the invention are, in general, carried out in a solvent comprising a polar organic solvent, and optionally including water. Catalyst or reaction systems of the invention comprise the catalysts described above in a solvent, to which the acid and alkene or alkyne may be added to carry out the reaction. Depending on the choice of catalysts, in some embodiments the catalyst systems are free of transition metal catalysts. The catalysts may be provided in an equimolar amount any suitable molar ratio; e.g., from 1:100 or 1:50 to 50:1 or 100:1.

Preferably, the systems are provided and the methods are carried out to the exclusion of oxygen. This may be achieved in accordance with known techniques, such as by filling the gas phase of the reaction vessel or blanketing the liquid phase with an inert, protective or noble gas such as nitrogen, helium or argon. See, e.g., U.S. Pat. Nos. 3,959,307; 5,604,919; and 5,777,146.

The solvent may be protic or aprotic. Examples of suitable solvents include, but are not limited to, ethanol, methanol, acetonitrile, and halogenated solvents such as chloroform, dichloromethane, dichloroethane, etc. Time, temperature and pressure is not critical, but in general the reactions may be carried out at a temperature of −100 or −70° C. up to 70 or 100° C.

Specific types of reactions that can be carried out by the methods of the present invention include, but are not limited to: intramolecular hydroalkoxylation reactions, intramolecular hydrolactonization reactions, intermolecular hydroacetoxylation reactions (and including intermolecular hydroamination, intermolecular hydrofluorination, and intermolecular hydrophosphatoxylation (e.g., the addition of a phosphoric acid across an alkene)), and anti-Markovnikov polymerization reactions where the acid and alkene group are contained within the same monomeric unit (e.g., to produce a homopolymer) or are contained on separate monomeric units (e.g., to produce a copolymer).

The present invention is explained in greater detail in the following non-limiting Examples.

EXAMPLES

The direct addition of N—H across an alkene[1] provides an efficient, atom-economical route to highly valuable, biologically active nitrogen containing compounds.[2] Considerable effort has been devoted to the development of catalyst systems for alkene hydroamination, with the majority of these strategies exhibiting preferential Markovnikov selectivity.[3,4] Thus, accessing anti-Markovnikov reactivity has proven quite challenging and considerably fewer reports exist in this arena. Catalytic intermolecular anti-Markovnikov olefin hydroamination reactions have been demonstrated using transition metals,[5] alkaline earth metals,[51] and to a limited extent, photosensitizers.[6,7] Notably, to our knowledge, there exists a single report of an intramolecular anti-Markovnikov hydroamination of styrenes reported by the Hartwig group in 2006 employing a Rh catalyst at elevated temperatures (eq. 1).[8,9] Recently, our group reported an anti-Markovnikov hydroalkoxylation reaction using a photocatalyst and hydrogen atom donor system.[10] Given the paucity of intramolecular anti-Markovnikov hydroamination reports, we saw an opportunity to further demonstrate the utility of our catalytic strategy towards this end. Here, we report a metal-free, anti-Markovnikov hydroamination of unsaturated amines using 9-mesityl-10-methylacridinium and thiophenol as a hydrogen atom donor (Scheme 1, eq. 2).

Scheme 1. Catalytic Anti-Markovnikov Intramolecular Hydroamination

Hartwig 2006:

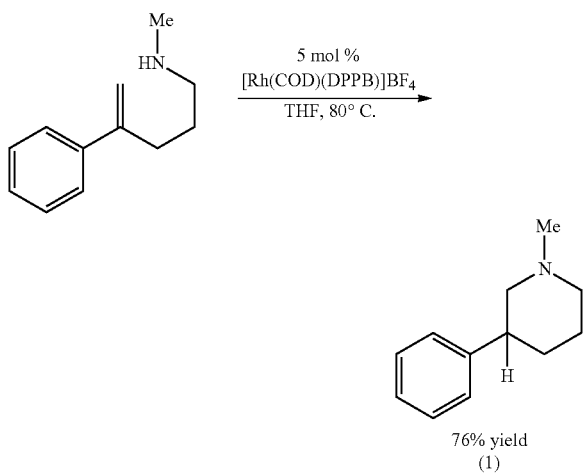

This Work:

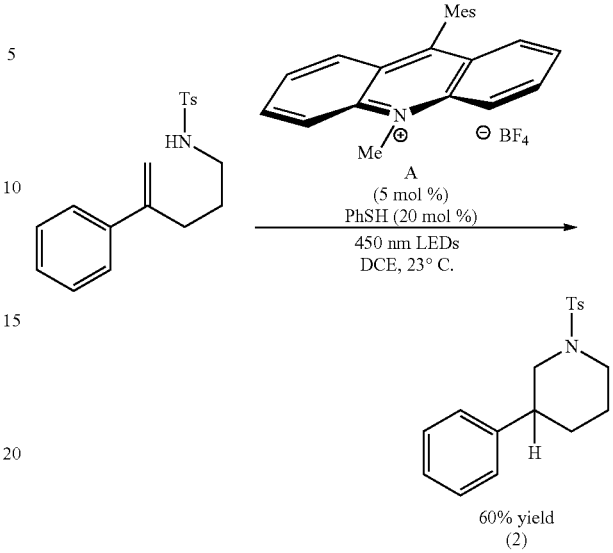

In our previously reported hydroalkoxylation reaction, we took advantage of the well-documented single electron oxidation of alkenes to provide unique radical cations that give rise to anti-Markovnikov reactivity.[11-13] We proposed to apply this strategy to the hydroamination reaction, although we anticipated some challenges associated with amine oxidation.[14] Sufficiently electron-rich amines are susceptible to oxidation at nitrogen and numerous groups have taken advantage of this reactivity.[15] While this pathway could lead to productive hydroamination, it may also result in undesirable side reactions stemming from amine cation radical intermediates. Judicious selection of the amine protecting group could circumvent these potential issues and for this reason, we elected to first examine the use of a sulfonyl group as it should be adequately withdrawing to suppress amine oxidation, yet still render the amine nucleophilic.

We began our studies by submitting the p-toluenesulfonyl-protected isoprenyl amine 9a to our previously reported conditions for the anti-Markovnikov hydroalkoxylation reaction. Despite the low yield obtained, complete anti-Markovnikov regioselection (>20:1) was observed in the formation of the desired pyrrolidine product after 3 days (16%, Table 1, entry 1). After additional efforts at reaction optimization (solvent, addition of organic and inorganic bases, concentration, etc.) failed to increase the reaction efficiency, we turned our attention to the identity of the hydrogen atom donor. While 9-cyanofluorene gave essentially the same result (entry 2) as did phenylmalononitrile, heteroatom hydrogen donor thiophenol provided a 2-fold increase in yield (entry 3). Upon decreasing the thiophenol loading to 20 mol %, we were pleased to find that pyrrolidine 9b could be obtained in a 70% yield as a single regioisomer (entry 4). To our knowledge, this result represents a rare example of an intramolecular anti-Markovnikov hydroamination of a non-activated olefin.[3b,4a]

Control experiments revealed that the thiophenol, light and photocatalyst were all necessary for productive reactivity (entries 8-10). The use of thiophenol as the hydrogen atom donor allowed us to explore the use of alternative common protecting groups for amines. While a benzyl protecting group afforded only small amounts of the pyrrolidine adduct (15% yield, entry 6), presumably due to the formation of numerous unidentified side products, we found that the Boc protecting group was suitable in this context (65% yield, entry 7). This supports our hypothesis that electron rich amines would be poor substrates as they are susceptible to oxidation. While the use of a Boc protecting group was quite appealing owing to the ease of its removal, we elected to evaluate tosylamine substrates for their straightforward characterization.

TABLE 1

Optimization Studies[a]

| Entry | R | H-Atom Donor | Time | Yield[b] |
|---|---|---|---|---|
| 1 | Ts | 1.0 equiv PhCH(CN)$_2$ | 72 | 16% |
| 2 | Ts | 1.0 equiv 9-Cyanofluorene | 72 | 12% |
| 3 | Ts | 1.0 equiv PhSH | 72 | 41% |
| 4 | Ts | 0.2 equiv PhSH | 96 | 70%[c] |
| 5 | H | 0.2 equiv PhSH | 96 | <5% |
| 6 | Bn | 0.2 equiv PhSH | 96 | 15% |
| 7 | Boc | 0.2 equiv PhSH | 96 | 65% |
| 8 | Ts | None | 96 | <5% |
| 9 | Ts | 0.2 equiv PhSH without photocatalyst | 24 | <5% |
| 10 | Ts | 0.2 equiv PhSH without light | 24 | <5% |

[a]All reactions irradiated with a 15 W 450 nm LED flood lamp.
[b]Determined by 1H NMR analysis.
[c]Isolated yield We next shifted our focus to the investigation of the alkene hydroamination reaction scope. Amine substrates bearing pendant styrenes underwent smooth 5-exo cyclization to furnish the corresponding regioisomerically pure pyrrolidines (entries 1-6). It should be noted that similar reactivity can be obtained with catalytic quantities of strong bases.[16] The presence of electron releasing (—OMe) and withdrawing (—F) groups had little effect on the reaction efficiencies (entries 2-5). Substitution at the ortho position of the styrene was tolerated, giving desired pyrrolidine 4b in 69% yield (entry 4). Importantly, 6-endo cyclizations of 1,1 disubstituted styrenes to give tolylpiperidine products 7b and 8b also proceeded in good yields and with complete regiocontrol (entry 7,8). We observed that geminal substitution in the backbone was not required for reactivity, and saw only slight decreases in yield as compared to their dimethyl substituted analogs, albeit longer reaction times were generally required (cf, entries 3&5; 7&8). For styrenyl substrates, the major byproduct was the cyclized deprotected product. Re-protection or deprotection of the reaction mixture can easily convert the remainder of the mass balance as desired.

Inclusion of a stereocenter neighboring the amino group (10a) gave stereocontrol during the ring-forming event, albeit in modest levels (3:1 d.r., entry 10). We were pleased to find that a more geometrically-challenging 5-endo cyclization could be achieved employing unsaturated amine 11a to afford the fully-saturated indole derivative 11b in 72% yield and 12:1 dr (entry 11). Furthermore, the method is not limited to tosylamine as the sulfamate proved to be a competent nucleophile, giving access to a unique 6-exo cyclization (entry 12).

From the beginning of our studies, we presumed that the role of the thiophenol was to act as a hydrogen atom donor and the subsequent thiyl radical could serve to reoxidize the reduced form of A. To exclude alternative mechanistic pathways, we conducted several control experiments. We considered that thiophenol could participate in a thiol-ene reaction that could be catalyzed by the acridinium catalyst.[17] Following the thiol-ene reaction, subsequent nucleophilic displacement of the resultant phenylthioether could furnish the observed products. However, this prospect seemed unlikely given that the limited examples of this reactivity require either strong exogenous base or elevated temperatures. To probe the potential involvement of this reaction pathway, we prepared Boc-protected unsaturated amine 13 and submitted it to the reaction conditions shown in eq 3. As we observed no incorporation of thiophenol into the molecule, we believe that the thiol-ene pathway is likely not operative in this transformation.

TABLE 2

Scope of the Intramolecular Anti-Markovnikov Hydroamination Reactions of Unsaturated Amines[a]

| Entry | Alkenol | Product | Time | Yield |
|---|---|---|---|---|
| 1 | 1a Ar = C$_6$H$_5$, R, R' = Me | 1b | 24 h | 82% |
| 2 | 2a Ar = 4-(F)C$_6$H$_4$, R, R' = Me | 2b | 24 h | 89% |
| 3 | 3a Ar = 4-(MeO)C$_6$H$_4$, R, R' = Me | 3b | 30 h | 88% |
| 4 | 4a Ar = 2-(MeO)C$_6$H$_4$, R, R' = Me | 4b | 40 h | 69% |

TABLE 2-continued

Scope of the Intramolecular Anti-Markovnikov Hydroamination Reactions of Unsaturated Amines[a]

| Entry | Alkenol | Product | Time | Yield |
|---|---|---|---|---|
| 5 | 5a Ar = 4-(MeO)C$_6$H$_4$, R, R' = H | 5b | 48 h | 79% |
| 6 | 6a Ar = 4-(MeO)C$_6$H$_4$, R = H, R' = i-Pr | 6b | 39 h | 88% 1.6:1 d.r.[b] |
| 7 | 7a R = Me | 7b | 48 h | 79% |
| 8 | 8a R = H | 8b | 96 h | 60% |
| 9 | 9a R = H; R' = Ph | 9b | 96 h | 70% |
| 10 | 10a R = Me; R' = H | 10b | 96 h | 56% 3:1 d.r.[b] |
| 11 | 11a | 11b | 96 h | 72% 12:1 d.r.[b] |
| 12 | 12a | 12b | 96 h | 54% |

[a]All reactions irradiated with a 15 W 450 nm LED flood lamp. Reported as isolated yields, average of two trials.
[b]Determined by $^1$H NMR analysis of the crude reaction mixtures.

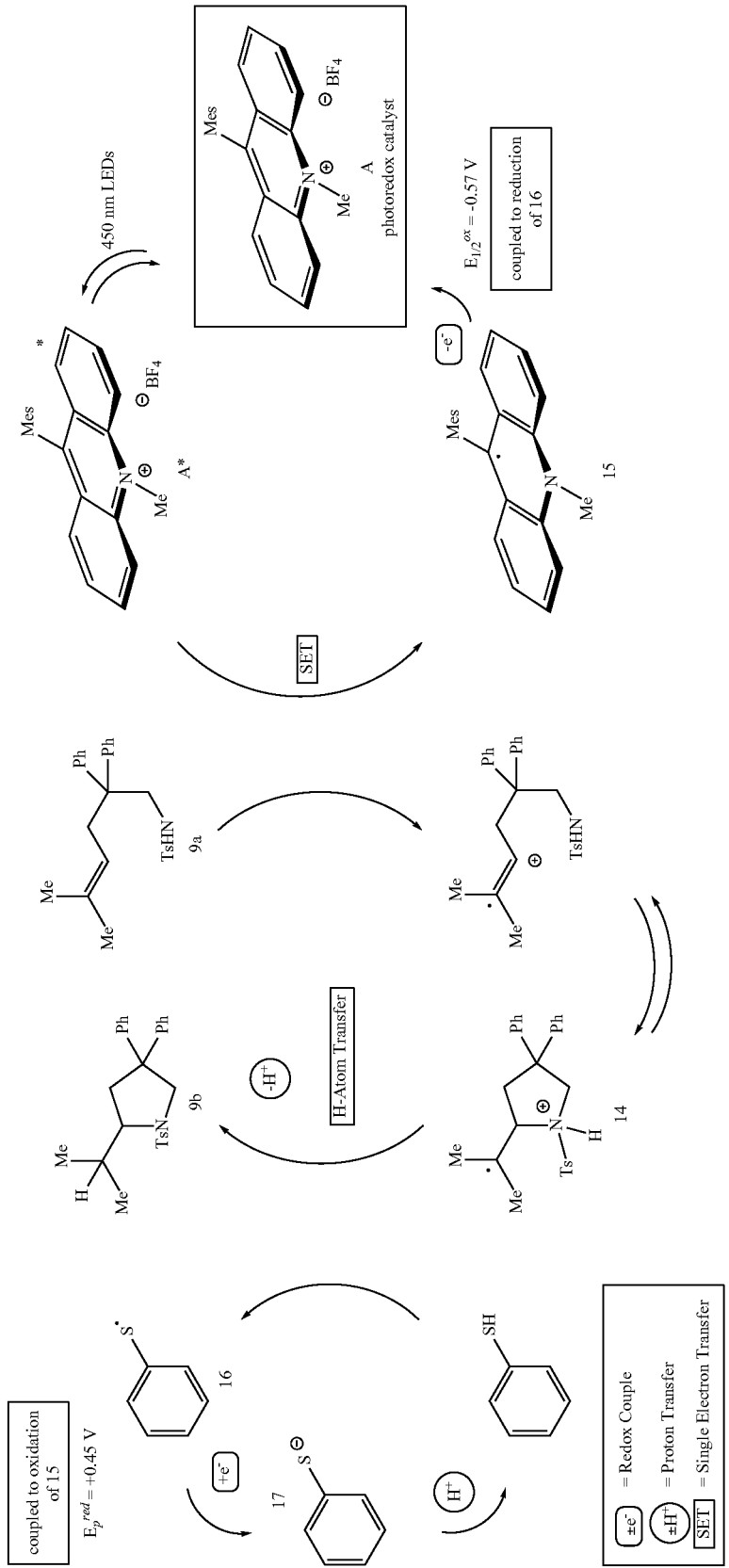
Scheme 2. Working Mechanism for Direct Anti-Markovnikov Hydroamination of Alkenes We also considered that thiophenol was acting solely as a hydrogen atom shuttle.[18] In this context, we submitted isoprenyl amine 9a to thiophenol with either di-tert-butyl peroxide or AIBN as thermal radical initiators (Conditions A and B, eq 4). No reactivity was observed in either case, suggesting that formation of nitrogen-centered radical intermediates was also unlikely.

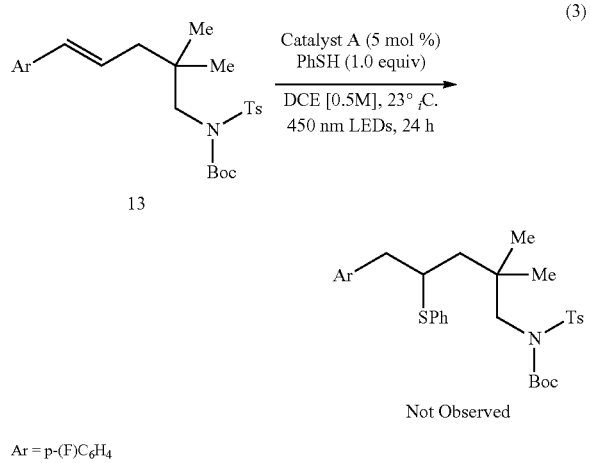

(3)

Ar = p-(F)C$_6$H$_4$

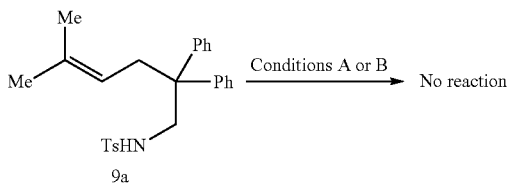

(4)

Conditions:
A) (t-BuO)$_2$ (0.5 equiv), PhSH (0.15 equiv), C$_6$H$_6$ [0.4M], 140 ,C., 96 h.
B) AIBN (0.2 equiv), PhSH (0.2 equiv), DCE [0.5M], 85 ,C., 96 h.

Finally, after the observation of varying quantities of PhSSPh in the crude reaction mixtures, we questioned whether this byproduct was active in the catalytic cycle. Subjection of 9a to the reaction conditions employing PhSSPh instead of PhSH afforded the anti-Markovnikov hydroamination product in 55% yield (eq 5). While this observation is not fully understood at this time, it is conceivable that diphenyl disulfide could serve as a reservoir of phenyl thiyl radical via oxidation of the disulfide ($E_p^{ox}$=+1.51 V vs. SCE)[19] and subsequent fragmentation. It is possible that the phenyl thiyl radical then can act as an oxidant for the reduced form of catalyst A in a manner similar to the mechanism invoked in our prior communication.[10]

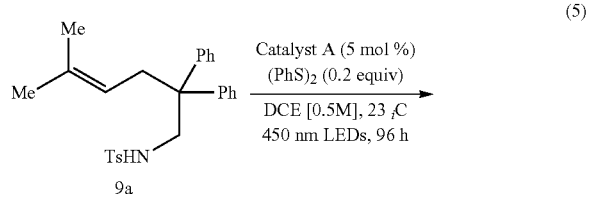

(5)

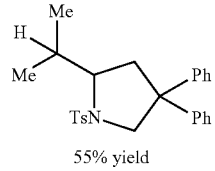

55% yield

Based on these experiments and the reactivity observed in this study, we have developed the working mechanistic hypothesis depicted in Scheme 2. After oxidation of the unsaturated amine (9a) by the excited state of the catalyst (A*), anti-Markovnikov addition of the amine would furnish intermediate cation radical 14. Hydrogen atom transfer from thiophenol to 14 would furnish the desired amine heterocycle (9a) after proton loss. The subsequent thiyl radical (15) could serve as an oxidant for 14 to reset catalyst A and generate thiophenoxide anion. Given the known reduction potential of 16 ($E_p$=+0.45 V vs. SCE)[20] and the oxidation potential of 15 ($E_{1/2}$=−0.57 V vs. SCE),[21] we estimate this electron transfer should be exergonic. Thiophenoxide then should serve as a mild base to neutralize the acid generated during the course of the reaction.

Experimental Details

General Methods: Infrared (IR) spectra were obtained using a Jasco 260 Plus Fourier transform infrared spectrometer. Proton and carbon magnetic resonance spectra (1H NMR and 13C NMR) were recorded on a Brukermodel DRX 400 ($^1$H NMR at 400 MHz and 600 MHz and $^{13}$C NMR at 100 MHz) spectrometer with solvent resonance as the internal standard (1H NMR: CDCl$_3$ at 7.24 ppm; 13C NMR: CDCl$^3$ at 77.0 ppm). $^1$H NMR data are reported as follows: chemical shift, multiplicity (s=singlet, d=doublet, t=triplet, dd=doublet of doublets, ddt=doublet of doublet of triplets, ddd=doublet of doublet of doublets, dddd=doublet of doublet of doublet of doublets m=multiplet, brs=broad singlet), coupling constants (Hz), and integration. Mass spectra were obtained using a Micromass (now Waters Corporation, 34 Maple Street, Milford, Mass. 01757) Quattro-II, Triple Quadrupole Mass Spectrometer, with a Z-spray nano-Electrospray source design, in combination with a NanoMate (Advion 19 Brown Road, Ithaca, N.Y. 14850) chip based electrospray sample introduction system and nozzle. Thin layer chromatography (TLC) was performed on SiliaPlate 250 µm thick silica gel plates provided by Silicycle. Visualization was accomplished with short wave UV light (254 nm) or cerium ammonium molybdate solution followed by heating. Flash chromatography was performed using SiliaFlash P60 silica gel (40-63 µm) purchased from Silicycle. Tetrahydrofuran, diethyl ether, dichloromethane, and toluene were dried by passage through a column of neutral alumina under nitrogen prior to use. Irradiation of photochemical reactions was carried out using a 15 W PAR38 blue LED floodlamp purchased from EagleLight (Carlsbad, Calif.). All other reagents were obtained from commercial sources and used without further purification unless otherwise noted.

Cyclic voltammograms were obtained with a glassy carbon working electrode, Ag/AgNO$_3$ reference electrode, a platinum wire auxiliary and a BAS CV-27 potentiostat using 1 mM solutions of analyte in acetonitrile with 0.1 M tetrabutylammonium hexafluorophosphate as supporting electrolyte at a scan rate of 0.1V/s. Oxidation potential is reported as the half-wave oxidation potential, taken as the midpoint between the onset of the sloping curve and the minima of the curve.

Preparation of Acridinium Photocatalyst (Catalyst A): The photocatalyst used in this study, N-Me-9-mesityl acridinium tetrafluoroborate, was synthesized by the method of Fukuzumi et al (Kotani, H.; Ohkubo, K.; Fukuzumi, S. *J. Am. Chem. Soc.* 2004, 126, 15999-16006). Tetrafluoroboric acid (diethyl ether complex) was substituted for perchloric acid during the hydrolysis. The spectral data matched the values reported in the literature for the perchlorate and hexafluorophosphate salts. $^1$H NMR (600 MHz, CDCl$_3$) δ 8.60 (d, J=9.0 Hz, 2H), 8.37 (t, J=9.0 Hz, 2H), 7.84 (s, 4H), 7.23 (s, 2H), 4.81 (s, 3H), 2.46 (s, 3H), 1.68 (s, 6H).

Oxidation Potentials of Substrates Vs. Ag/AgNO$_3$:

| Substrate | $E_{p/2}$ |
|---|---|
| (structure) | 1.23 V |
| (structure) | 0.77 V |
| (structure) | 1.31 V |
| (structure) | 1.44 V |
| (structure) | 0.77 V |
| (structure) | 1.29 V |
| (structure) | 1.04 V |
| (structure) | 1.27 V |
| (structure) | 1.03 V |
| (structure) | 1.38 V |
| (structure) | 0.88 V |
| (structure) | 1.31 V |
| (structure) | 0.83 V |
| (structure) | 1.32 V |
| (structure) | 1.02 V |

Preparation of Unsaturated Amine Substrates:

General Procedure A: Protection of Primary Amines with Tosylchloride

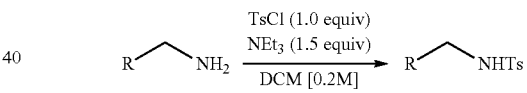

To a clean dry RBF was added a magnetic stir bar and the primary amine (1 equiv) under nitrogen at RT. Dissolved in DCM [0.2 M] and freshly distilled triethylamine (1.5 equiv) then tosylchloride added. Allowed to stir at room temperature overnight, then H$_2$O added and aqueous layer was extracted 3× with DCM, organic layers washed with brine solution, dried over Na$_2$SO$_2$ and concentrated in vacuo. Final substrates were purified by silica gel chromatography using the conditions listed.

4-Methyl-N-(5-methyl-2,2-diphenylhex-4-en-1-yl) benzenesulfonamide (9a)

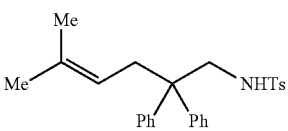

Prepared via general procedure A from 5-methyl-2,2-diphenylhex-4-en-1-amine (prepared according to Crimmin, M. R. et al., *J. Am. Chem. Soc.* 2009, 131, 9670-9685). Purified in 10% EtOAc/Hex to give a white solid in 51% yield. $^1$H NMR (400 MHz, CDCl$_3$) δ=7.57 (d, J=8.0 Hz, 2

H), 7.33-7.16 (m, 8H), 7.11-7.02 (m, 4 H), 4.77-4.69 (m, 1 H), 3.87 (t, J=6.1 Hz, 1 H), 3.50 (d, J=6.3 Hz, 2 H), 2.81 (d, J=7.0 Hz, 2 H), 2.42 (s, 3 H), 1.58-1.53 (m, 3 H), 1.38 (s, 3 H); $^{13}$C NMR (100 MHz, CDCl$_3$) δ=144.8, 143.4, 136.1, 135.5, 129.7, 128.1, 127.2, 126.6, 118.5, 50.2, 49.7, 35.6, 26.0, 21.5, 17.9; IR (thin film): 3276, 3058, 2919, 1671, 1598, 1496, 1445, 1406, 1330, 1266 cm$^{-1}$; LRMS (ESI): Calculated for [M+H$_+$]=420.58. found 420.26.

N-Benzyl-5-methyl-2,2-diphenylhex-4-en-1-amine
(Table 1, entry 6)

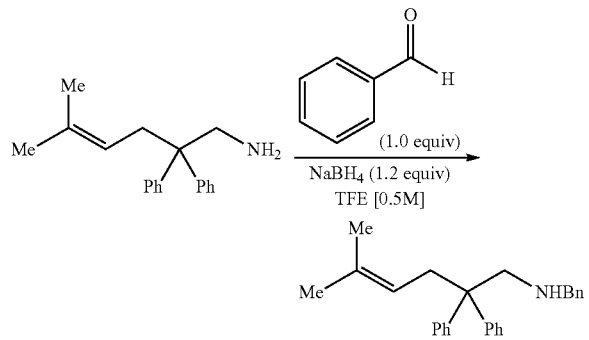

To a clean dry RBF was added a magnetic stir bar, 5-methyl-2,2-diphenylhex-4-en-1-amine (1.0 equiv, prepared according to Crimmin, M. R. et al., *J. Am. Chem. Soc.*, 2009, 131, 9670-9685) and benzaldehyde (1.0 equiv), dissolved in TFE [0.5 M] under nitrogen. Reaction mixture was heated to 40° C. for ~1 h then sodium borohydride was added. Allowed to stir at 40° C. for ~3 h then heating was discontinued, reaction mixture was filtered through cotton then concentrated in vacuo. Title compound was purified by silica gel chromatography using 10% EtOAc/Hexanes to give a colorless oil in 56% yield. $^1$H NMR (400 MHz, CDCl$_3$) δ=7.33-7.18 (m, 5 H), 7.18-7.12 (m, 5 H), 4.76-4.69 (m, 1 H), 3.69 (s, 2 H), 3.15 (s, 2 H), 2.92 (d, J=7.3 Hz, 2 H), 1.53 (s, 3 H), 1.46 (s, 3 H); $^{13}$C NMR (100 MHz, CDCl$_3$) δ=147.3, 140.8, 134.0, 128.3, 127.9, 126.7, 125.9, 120.4, 55.7, 54.3, 50.9, 35.8, 26.0, 17.9; IR (thin film): 3065, 3058, 3025, 2966, 2912, 2852, 2359, 1943, 1868, 1800, 1749, 1716, 1698, 1683, 1670, 1540, 1495, 1444, 1375, 1361 cm$^{-1}$; LRMS (ESI): Calculated for [M+H$^+$]=356.52. found 356.19.

tert-Butyl (5-methyl-2,2-diphenylhex-4-en-1-yl)
carbamate (Table 1, entry 7)

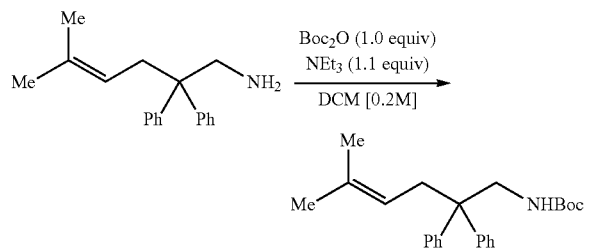

To a clean dry RBF was added a magnetic stir bar and 5-methyl-2,2-diphenylhex-4-en-1-amine (1.0 equiv, prepared according to Crimmin, M. R. et al., *J. Am. Chem. Soc.* 2009, 131, 9670-9685) and dissolved in DCM [0.2 M] under nitrogen. Reaction mixture was cooled to −78° C. and freshly distilled triethylamine added then boc anhydride added quickly. Allowed to stir at −78° C. for ~30 min then warmed to 0° C. After 1 h, saturated ammonium chloride solution was added, the aqueous layer was extracted 3× with DCM, organic layers were combined and washed with brine solution, dried over Na$_2$SO$_4$ and concentrated in vacuo. Purified via silica gel chromatography with 10% EtOAc/Hexanes to give the desired product as a white solid in 68% yield. $^1$H NMR (400 MHz, CDCl$_3$) δ=7.30-7.24 (m, 4 H), 7.22-7.11 (m, 6 H), 4.82 (t, J=6.8 Hz, 1 H), 4.12 (br. s., 1 H), 3.80 (d, J=5.9 Hz, 2 H), 2.77 (d, J=7.1 Hz, 2 H), 1.56 (s, 3 H), 1.39 (s, 3 H), 1.35 (s, 9 H); $^{13}$C NMR (100 MHz, CDCl$_3$) δ=155.8, 145.7, 134.8, 128.2, 126.3, 119.3, 50.8, 47.4, 35.9, 28.4, 27.4, 26.0, 17.7; JR (thin film): 3442, 2925, 1718, 1498, 1445, 1390, 1365, 1233 cm$^{-1}$; LRMS (ESI): Calculated for [M+H$^+$]=366.51. found 366.24.

General Procedure B: Preparation of N-Tosylamines Via Amide Coupling/Reduction Sequence

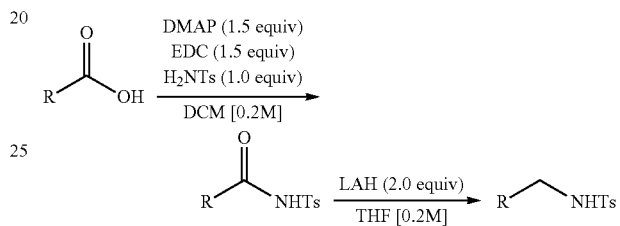

To a clean dry RBF was added a magnetic stir bar, the starting carboxylic acid (1.0 equiv), dimethylaminopyridine (1.5 equiv) and tosylamine (1.0 equiv) under nitrogen at ambient temperature. Dissolved in DCM [0.2 M] then EDC (1.5 equiv) was added. Reaction was stirred at RT overnight. Then 4N HCl was added, phases were separated then aqueous layer extracted three times with DCM. Organic portions were combined and washed with brine solution, dried over Na$_2$SO$_4$ and concentrated in vacuo. Reaction mixtures were then taken onto the reduction step as a crude reaction mixture.

To a clean dry RBF was added a magnetic stir bar, the starting amide (1.0 equiv) and lithium aluminium hydride (2.0 equiv) under nitrogen. Reaction was cooled to 0° C. and slowly dissolved in THF [0.2 M]. Reaction was monitored by TLC and upon complete consumption of starting material, mixture was cooled to 0° C. and a saturated solution of sodium potassium tartrate was added slowly. The reaction was allowed to warm to RT and stirred for ~20 min. Then phases were separated and aqueous layer extracted three times with diethyl ether, and organic layers combined and washed with brine solution. Dried over Na$_2$SO$_4$ and concentrated in vacuo. Final substrates were purified by silica gel chromatography using the conditions listed.

(E)-N-(2,2-Dimethyl-5-phenylpent-4-en-1-yl)-4-methylbenzenesulfonamide (1a)

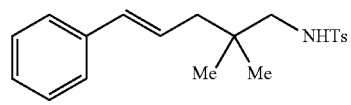

Prepared using general procedure B starting from (E)-2,2-dimethyl-5-phenylpent-4-enoic acid$_3$ (prepared according to Hamilton, D. S.; Nicewicz, D. A. *J. Am. Chem. Soc.* 2012, 134, 18577-18580). Title compound was purified in 10% EtOAc/Hexanes to give a white solid in 33% yield over two steps. The alkenol was found as a major by-product. $^1$H NMR (400 MHz, CDCl$_3$) δ=7.75 (d, J=8.3 Hz, 2 H), 7.30-7.16 (m, 7 H), 6.34 (d, =15.6 Hz, 1 H), 6.15-6.04 (m, 1 H), 5.02 (t, 6.8 Hz, 1 H), 2.70 (d, J=7.0 Hz, 2 H), 2.37 (s, 3 H), 2.10 (d, J=7.5 Hz, 2 H), 0.90 (s, 6 H); $^{13}$C NMR (100 MHz, CDCl$_3$) δ=143.3, 137.5, 137.0, 133.0, 129.7, 128.5, 127.1, 126.1, 52.8, 42.9, 34.8, 25.1, 21.5; IR (thin film): 3275, 3025, 2956, 1653, 1597, 1576, 1493, 1457, 1410, 1368, 1321, 1265 cm$^{-1}$; LRMS (ER): Calculated for [M+H$^+$]=344.48. found 344.24.

(E)-N-(5-(4-Fluorophenyl)-2,2-dimethylpent-4-en-1-yl)-4-methylbenzenesulfonamide (2a)

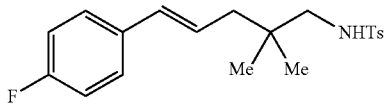

Prepared using general procedure B starting from (E)-5-(4-fluorophenyl)-2,2-dimethylpent-4-enoic acid (prepared according to Hamilton, D. S.; Nicewicz, D. A. *J. Am. Chem. Soc.* 2012, 134, 18577-18580). Title compound was purified in 10% EtOAc/Hexanes to give a white solid in 33% yield over two steps. The alkenol was found as a major by-product. $^1$H NMR (400 MHz, CDCl$_3$) δ=7.72-7.68 (dd, 2 H), 7.28-7.22 (m, 4 H), 6.96 (dd, J=8.7 Hz, 2 H), 6.30 (d, J=16.1 Hz, 1 H), 6.06-5.96 (m, 1 H), 4.34-4.27 (m, 1 H), 2.71 (d, J=7.0 Hz, 2 H), 2.39 (s, 3 H), 2.11-2.07 (m, 2 H), 0.89 (s, 6 H); $^{13}$C NMR (100 MHz, CDCl$_3$) δ=163.2, 160.8, 143.3, 137.0, 133.7, 131.8, 129.7, 127.4, 125.8, 115.4, 115.2, 52.7, 42.8, 34.8, 25.1, 21.5; IR (thin film): 3284, 3031, 2961, 1652, 1600, 1508, 1471, 1417, 1325, 1266, 1227 cm$^{-1}$; LRMS (ESI): Calculated for [M+H$_+$]=362.47. found 362.04.

(E)-N-(5-(4-Methoxyphenyl)-2,2-dimethylpent-4-en-1-yl)-4-methylbenzenesulfonamide (3a)

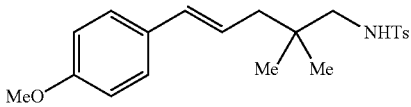

Prepared using general procedure B starting from (E)-5-(4-methoxyphenyl)-2,2-dimethylpent-4-enoic acid (prepared according to Hamilton, D. S.; Nicewicz, D. A. *J. Am. Chem. Soc.* 2012, 134, 18577-18580). Title compound was purified in 10% EtOAc/Hexanes to give a white solid in 25% yield over two steps. The alkenol was found as a major by-product. $^1$H NMR (400 MHz, CDCl$_3$) δ=7.77 (d, 8.3 Hz, 2 H), 7.32-7.27 (m, 2 H), 7.25 (d, J=8.5 Hz, 2 H), 6.85 (d, J=8.5 Hz, 2 H), 6.31 (d, 15.6 Hz, 1 H), 6.04-5.92 (m, 1 H), 4.91 (t, J=. 6.8 Hz, 1 H), 3.82 (s, 3 H), 2.73 (d, J=7.0 Hz, 2 H), 2.42 (s, 3 H), 2.11 (d, J=7.5 Hz, 2 H), 0.92 (s, 6 H); $^{13}$C NMR (100 MHz, CDCl$_3$) δ=158.9, 143.3, 136.9, 132.3, 130.3, 129.7, 127.2, 123.7, 113.9, 55.6, 52.8, 42.9, 34.8, 25.1, 21.5, 19.9; IR (thin film): 3283, 3030, 2960, 2836, 1770, 1651, 1607, 1576, 1509, 1465, 1419, 1368, 1325, 1247 cm$^{-1}$; LRMS (ESI): Calculated for [M+H$^+$]=374.51. found 374.22.

(E)-N-(5-(2-Methoxyphenyl)-2,2-dimethylpent-4-en-1-yl)-4-methylbenzenesulfonamide (4a)

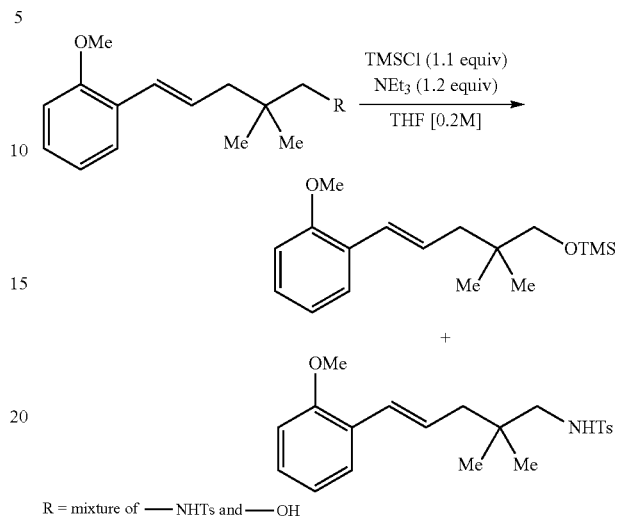

R = mixture of ——NHTs and ——OH

Prepared using general procedure B starting from (E)-5-(2-methoxyphenyl)-2,2-dimethylpent-4-enoic acid (prepared according to Hamilton, D. S.; Nicewicz, D. A. *J. Am. Chem. Soc.* 2012, 134, 18577-18580). Desired product was obtained as an inseparable mixture with the alkenol by-product. To a clean dry RBF was added a magnetic star bar and the amine/alcohol mixture and dissolved in THF [0.2 M] under nitrogen. Then freshly distilled triethylamine (1.2 equiv) and TMSCl (1.1 equiv) added and allowed to stir overnight at room temperature. Then H$_2$O was added and layers separated. The aqueous layer was extracted 3× with Et$_2$O, organic layers combined and washed with brine solution, dried over Na$_2$SO$_4$ and concentrated in vacuo. Purified by silica gel chromatography with 25% EtOAc/Hexanes to give the title compound In 19% yield over three steps. $^1$H NMR (400 MHz, CDCl$_3$) δ 7.72 (d, J=8.1 Hz, 2 H), 7.30 (dd, J=1.5, 7.6 Hz, 1 H), 7.23-7.14 (m, 3 H), 6.91-6.81 (m, 2 H), 6.65 (d, J=15.9 Hz, 1 H), 6.13-6.03 (m, 1 H), 4.79 (t, J=6.8 Hz, 1 H), 3.81 (s, 3 H), 2.70 (d, J=6.8 Hz, 2 H), 2.38-2.35 (m, 3 H), 2.11 (d, J=7.6 Hz, 2 H), 0.90 (s, 6 H); $^{13}$C NMR (100 MHz, CDCl$_3$) δ=156.4, 143.3, 137.0, 129.7, 128.2, 127.7, 127.1, 126.8, 126.6, 126.5, 120.6, 110.9, 55.5, 52.9, 43.6, 34.8, 25.2, 21.5; IR (thin film): 3283, 2960, 1715, 1488, 1463, 1436, 1327, 1242 cm$^{-1}$; LRMS (ESI): Calculated for [M+H$_+$]=374.51. found 374.16.

(E)-N-(5-(4-Methoxyphenyl)pent-4-en-1-yl)-4-methylbenzenesulfonamide (5a)

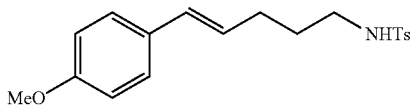

Prepared via general procedure A from (E)-5-(4-methoxyphenyl)pent-4-en-1-amine (prepared according to Schlummer, B.; Hartwig, J. F. *Org. Lett.* 2002, 4, 1471-1474). Purified by silica gel chromatography in 15% EtOAc/Hex to give a colorless oil in 25% yield. $_1$H NMR (cis) (400 MHz, CDCl$_3$) δ=7.69 (d, J=8.3 Hz, 2 H), 7.28-7.22 (m, 2 H), 7.12 (d, 8.5 Hz, 2 H), 6.87-6.81 (m, 2 H), 6.32 (d, J=11.5 Hz, 1 H), 5.41 (td, J=7.2, 11.6 Hz, 1 H), 4.66 (t, J=6.1 Hz, 1 H), 3.78 (s, 3 H), 2.93 (qd, J=6.7, 13.0 Hz, 2 H), 2.38 (s, J=2.3 Hz, 3 H), 2.27 (dq, J=1.5, 7.4 Hz, 2 H), 1.63-1.54 (m, 2 H) $^1$H NMR (trans) (400 MHz, CDCl$_3$) δ=7.73 (d, J=8.3 Hz, 2 H), 7.28-7.23 (m, 2 H), 7.19 (d, J=8.8 Hz, 2 H), 6.81-6.76 (m, 2 H), 6.23 (d, J=15.8 Hz, 1 H), 5.95-5.84 (m, 1 H), 4.77 (t, J=6.1 Hz, 1 H), 3.77 (s, 3 H), 2.98-2.92 (m, 2 H), 2.38 (s, 3 H), 2.19-2.11 (m, 2 H), 1.67-1.57 (m, 2 H); $^{13}$C NMR (mix of isomers) (100 MHz, CDCl$_3$) δ=143.4, 137.0, 130.3, 130.0, 129.7, 129.4, 127.9, 127.0, 113.9, 113.7, 55.3, 42.9, 42.6, 29.8, 29.3, 25.6, 21.5; IR (thin film): 3280, 3005, 2933, 1607, 1575, 1509, 1456, 1323 cm$^{-1}$; LRMS (ESI): Calculated for [M+H$^+$]=346.46. found 346.11.

(E)-N-(2-Isopropyl-5-(4-methoxyphenyl)pent-4-en-1-yl)-4-methylbenzenesulfonamide (6a)

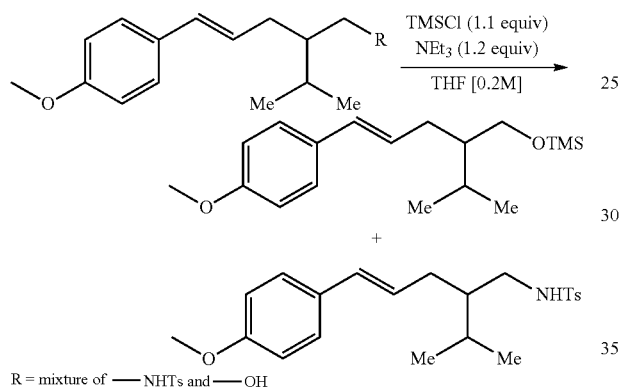

R = mixture of ──NHTs and ──OH

Prepared using general procedure B starting from (E)-2-isopropyl-5-(4-methoxyphenyl)pent-4-enoic acid (prepared according to Hamilton, D. S.; Nicewicz, D. A. J. Am. Chem. Soc. 2012, 134, 18577-18580). Desired product was obtained as an inseparable mixture with the alkenol. To a clean dry RBF was added a magnetic star bar and the amine/alcohol mixture and dissolved in THF [0.2 M] under nitrogen. Then freshly distilled triethylamine (1.2 equiv) and TMSCl (1.1 equiv) added and allowed to stir overnight at room temperature. Then H$_2$O was added and layers separated. The aqueous layer was extracted 3× with Et$_2$O, organic layers combined and washed with brine solution, dried over Na$_2$SO$_4$ and concentrated in vacuo. Purified by silica gel chromatography with 20% EtOAc/Hexanes to give the title compound in 18% yield over three steps. $^1$H NMR (400 MHz, CDCl$_3$) δ=7.67 (d, J=8.3 Hz, 2 H), 7.20 (t, J=8.6 Hz, 4 H), 6.82 (d, 8.6 Hz, 2 H), 6.24 (d, J=16.4 Hz, 1 H), 5.87 (td, J=7.6, 15.5 Hz, 1 H), 4.27 (br. s., 1 H), 3.79 (s, 3 H), 2.98-2.81 (m, 2 H), 2.37 (s, 3 H), 2.28-2.19 (m, 1 H), 2.07-1.98 (m, 1 H), 1.73 (dd, J=6.5, 12.1 Hz, 1 H), 1.48-1.37 (m, 1 H), 0.86 (d, J=3.7 Hz, 3 H), 0.84 (d, J=3.7 Hz, 3 H); $^{13}$C NMR (100 MHz, CDCl$_3$) δ=158.8, 143.2, 136.9, 131.1, 130.3, 129.7, 127.1, 126.4, 113.9, 55.3, 44.4, 44.0, 32.3, 28.2, 21.5, 19.6, 19.2; IR (thin film): 3648, 3566, 3283, 3030, 2958, 2933, 2873, 2737, 1918, 1770, 1716, 1652, 1607, 1576, 1510, 1464, 1325, 1440, 1419, 1388, 1368, 1325, 1304, 1289 cm$^{-1}$; LRMS (EST): Calculated for [M+H$^+$]=387.54. found 388.13.

N-(3,3-Dimethyl-4-phenylpent-4-en-1-yl)-4-methyl-benzenesulfonamide (7a)

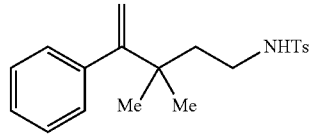

Prepared using general procedure B starting from 3,3-dimethyl-4-phenylpent-4-enoic acid[3] (prepared according to Hamilton, D. S.; Nicewicz, D. A. J. Am. Chem. Soc. 2012, 134, 18577-18580). Title compound was purified by silica gel chromatography in 25% EtOAc/Hexanes to give a white solid in 45% yield over two steps. $^1$H NMR (400 MHz, CDCl$_3$) δ=7.73 (d, J=8.3 Hz, 2 H), 7.31-7.26 (m, 2 H), 7.22-7.17 (m, 3 H), 6.96 (dd, J=3.0, 6.5 Hz, 2 H), 5.06 (d, J=1.5 Hz, 1 H), 4.82 (d, J=1.3 Hz, 1 H), 4.67 (t, J=6.0 Hz, 1 H), 3.01-2.93 (m, 2 H), 2.41 (s, 3 H), 1.53-1.47 (m, 2 H), 1.02 (s, 6 H); $_{13}$C NMR (100 MHz, CDCl$_3$) δ=156.7, 143.4, 142.6, 137.0, 129.7, 128.7, 127.6, 126.9, 114.2, 40.2, 40.0, 38.4, 27.8, 21.6; IR (thin film): 3279, 3080 3053, 2967, 2871, 1810, 1717, 1625, 1598, 1573, 1493, 1439, 1362, 1325, 1267, 1230 cm$^{-1}$; LRMS (ESI): Calculated for [M+H$^+$]=344.48. found 344.18.

4-Methyl-N-(4-phenylpent-4-en-1-yl)benzenesulfonamide (8a)

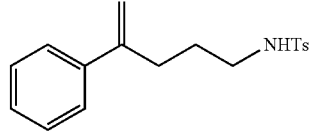

Prepared using general procedure B starting from 4-phenylpent-4-enoic acid[3] (prepared according to Hamilton, D. S.; Nicewicz, D. A. J. Am. Chem. Soc. 2012, 134, 18577-18580). Title compound was purified by silica gel chromatography in 20% EtOAc/Hexanes to give a white solid in 56% yield over two steps. Spectral data were in agreement with literature values.[5] (Zhou, L. et al., J. Am. Chem. Soc. 2011, 133, 9164-9167). $^1$H NMR (400 MHz, CDCl$_3$) δ=7.73-7.64 (m, 2 H), 7.31-7.15 (m, 5 H), 5.22-5.15 (m, 1 H), 4.95 (t, J=6.0 Hz, 1 H), 4.93 (s, 1 H), 2.87 (q, J=6.8 Hz, 2 H), 2.50-2.39 (m, 2 H), 2.34 (s, 3 H), 1.59-1.47 (m, 2 H).

4-Methyl-N-(6-methylhept-5-en-2-yl)benzenesulfonamide (10a)

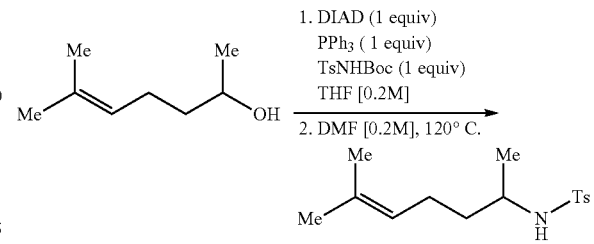

To a clean dry RBF was added a magnetic stir bar, tosylboc amine and triphenylphosphine and solids were dissolved in THF [0.2 M] under nitrogen. Then 6-methyl-hept-5-en-2-ol (commercially available) was added and reaction was cooled to 0° C. and then DIAD was added and allowed to warm to RT overnight. Then Et$_2$O was added and aqueous layer was extracted 3× with Et$_2$O, organic layers were combined and washed with brine solution, dried over Na$_2$SO$_4$ and concentrated in vacuo. Purified by silica gel chromatography in 10% EtOAc/Hexanes.

To a clean dry vial was added a magnetic stir bar, tosylboc amine and dissolved in DMF [0.2 M] under nitrogen. The vial was sealed and heated to 120° C. for 48 hours. Heating was discontinued and H$_2$O was added and then the aqueous layer was extracted 3× with Et$_2$O, organic layers were combined and washed with brine solution, dried over Na$_2$SO$_4$ and concentrated in vacuo. Purified by silica gel chromatography in 10% EtOAc/Hexanes to give the title compound as a colorless oil in 27% yield over 2 steps. Spectral data were in agreement with literature values.[6] (Marcotullio, M.; et al., *Synthesis* 2006, 2006, 2760-2766). $^1$H NMR (400 MHz, CDCl$_3$) δ=7.77-7.72 (m, 2 H), 7.25 (d, J=8.3 Hz, 2 H), 4.91-4.85 (m, 2 H), 3.31-3.19 (m, 1 H), 2.38 (s, 3 H), 1.96-1.74 (m, 2 H), 1.59 (s, 3 H), 1.47 (s, 3 H), 1.38-1.30 (m, 2 H), 1.00 (d, J=6.5 Hz, 3 H).

N-(2-(Cyclohex-1-en-1-yl)ethyl)-4-methylbenzene-sulfonamide (11a)

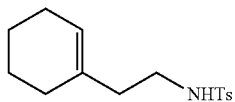

Prepared via general procedure A from commercially available 2-(cyclohex-1-en-1-yl)ethanamine. Purified in 10% EtOAc/Hex to give a white solid in 27% yield. Spectral data were in agreement with literature values.[6] $^1$H NMR (400 MHz, CDCl$_3$) δ=7.71 (d, J=8.3 Hz, 2 H), 7.30-7.24 (m, 2 H), 5.33 (br. s., 1 H), 4.58 (t, J=5.6 Hz, 1 H), 2.95 (q, J=6.5 Hz, 2 H), 2.39 (s, 3 H), 2.01 (t, J=6.7 Hz, 2 H), 1.94-1.86 (m, 2 H), 1.68 (br. s., 2 H), 1.54-1.41 (m, 4 H).

(E)-4-Phenylbut-3-en-1-yl sulfamate (12a)

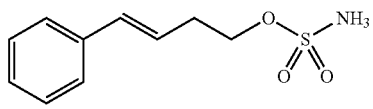 [SMILES: NS(=O)(=O)OCC/C=C/c1ccccc1]

Prepared according to a published procedure;[7] (Espino, C. G. et al., *J. Am. Chem. Soc.* 2001, 123, 6935-6936); spectral data were in agreement with literature values.[8] (Estéoule, A., et al., *Synthesis* 2007, 2007, 1251-1260). $^1$H NMR (400 MHz, CDCl$_3$) δ 7.42-7.28 (m, 4 H), 7.27-7.20 (m, 1 H), 6.50 (d, J=15.9 Hz, 1 H), 6.16 (td, J=7.0, 15.8 Hz, 1 H), 5.15 (s, 2 H), 4.28 (t, J=6.6 Hz, 2 H), 2.63 (q, J=6.6 Hz, 2 H)

(E)-tert-Butyl (5-(4-fluorophenyl)-2,2-dimethylpent-4-en-1-yl)(tosyl)carbamate (13)

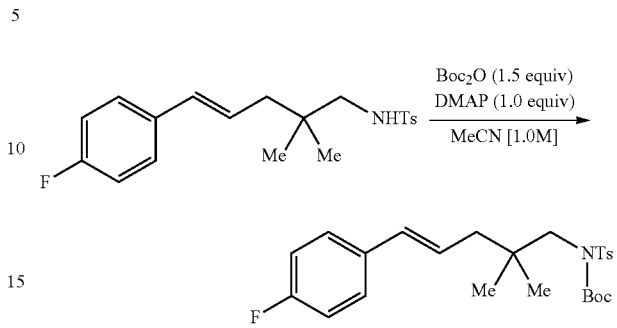

To a clean dry RBF was added a magnetic stir bar and (E)-N-(5-(4-fluorophenyl)-2,2-dimethylpent-4-en-1-yl)-4-methylbenzenesulfonamide (1.0 equiv) and DMAP (1.0 equiv) and dissolved in MeCN [1.0 M] under nitrogen. Then boc anhydride was added quickly. Allowed to stir at RT overnight. Water was added, and the aqueous layer extracted 3× with EtOAc, organic layers combined and washed with 1M HCl solution then brine solution, dried over Na$_2$SO$_4$ and concentrated in vacuo. Purified via silica gel chromatography with 10% EtOAc/Hexanes to give the desired product as a colorless oil in 64% yield. $^1$H NMR (400 MHz, CDCl$_3$) δ=7.73-7.68 (m, 2 H), 7.34-7.25 (m, 4 H), 6.99-6.93 (m, 2 H), 6.40-6.32 (m, 1 H), 6.25-6.15 (m, 1 H), 3.87 (s, 2 H), 2.41 (s, 3 H), 2.22 (d, J=7.3 Hz, 2 H), 1.22 (s, 9 H), 1.02 (s, 6 H); $^{13}$C NMR (100 MHz, CDCl$_3$) δ=151.6, 144.0, 137.9, 133.9, 131.5, 129.3, 127.6, 126.6, 115.4, 115.2, 84.1, 56.2, 44.2, 36.7, 27.6, 25.3, 21.6; IR (thin film): 3674, 3648, 3028, 3617, 3566, 3437, 3039, 2979, 2932, 2825, 2392, 1808, 1730, 1652, 1636, 1599, 1588, 1508, 1472, 1434, 1395, 1354, 1276, 1225 cm$^{-1}$; LRMS (ESI): Calculated for [M+Na]=484.59. found 484.15.

General Procedure C: Anti-Markovnikov Hydroamination Reactions

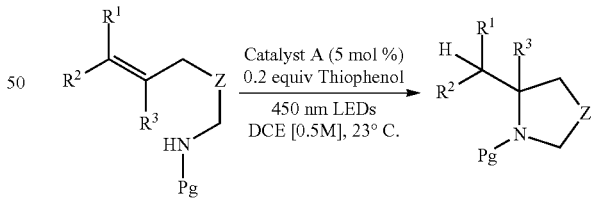

To a clean flame-dried 1 dram vial was added a magnetic stir bar, N-Me-mesityl acridinium catalyst (5.0 mol %) and protected amine substrate (100 mg). Reaction vessel was purged with nitrogen then dichloroethane (sparged for 15 min, [0.5M]) was added, then thiophenol (0.2 equiv). Reaction was sealed with Teflon tape then irradiated with blue LED lamp at room temperature until reaction was complete monitoring by TLC. Reactions were quenched with a solution of TEMPO (~5 mg) in dichloromethane (0.2 mL) and concentrated in vacuo. The final products were purified by silica gel chromatography using the conditions listed.

2-Isopropyl-4,4-diphenylpyrrolidine

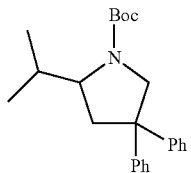 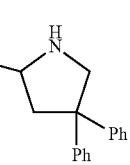

DCM:TFA (1:1)

Prepared using general procedure C on a 100 mg scale with 0.2 equiv thiophenol, and dichloroethane [0.5 M]. Irradiated for 96 h then purified in 3% EtOAc/Hexanes to give a white solid in 65% isolated yield. $^1$H NMR was very complex, to confirm identity isolated material was submitted to deprotection with TFA.

To a clean dry RBF was added a magnetic stir bar and tert-butyl 2-isopropyl-4,4-diphenylpyrrolidine-1-carboxylate and dissolved in DCM:TFA (1:1) under nitrogen at room temperature. After 3 h, saturated sodium bicarbonate added, aqueous layer extracted 3× with DCM, organic layers combined and washed with brine solution, dried over na2SO4 and concentrated in vacuo. Purified by silica gel chromatography in 50% EtOAc/Hexanes to give the desired 2-isopropyl-4,4-diphenylpyrrolidine. Spectral data were in agreement with literature values.[9] (Chapurina, Y. et al., *J. Org. Chem.* 2011, 76, 10163-10172). $^1$H NMR (400 MHz, CDCl$_3$) δ=7.33-7.24 (m, 4 H), 7.23-7.11 (m, 6 H), 3.73 (dd, J=1.7, 11.2 Hz, 1 H), 3.33 (d, J=11.2 Hz, 1 H), 2.90-2.82 (m, 1 H), 2.70 (ddd, J=1.7, 6.5, 12.6 Hz, 1 H), 2.06 (dd, J=9.8, 12.7 Hz, 1 H), 1.71-1.60 (m, 1 H), 1.28 (d, J=16.1 Hz, 1 H), 0.94 (d, J=6.6 Hz, 3 H), 0.88 (d, J=6.6 Hz, 3 H)

2-Benzyl-4,4-dimethyl-1-tosylpyrrolidine (1b)

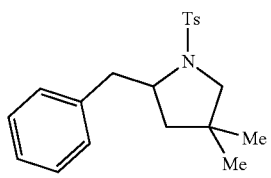 [SMILES: Cc1ccc(S(=O)(=O)N2CC(C)(C)CC2Cc2ccccc2)cc1]

Prepared using general procedure C on a 100 mg scale with 0.2 equiv thiophenol, and dichloroethane [0.5 M]. Irradiated for 24 h then purified in 2% EtOAc/Hexanes to give a white solid in 82% isolated yield (average of two trials). $^1$H NMR (400 MHz, CDCl$_3$) δ=7.79 (d, J=8.0 Hz, 2H), 7.33 (d, 8.3 Hz, 2 H), 7.29 (d, J=7.3 Hz, 2 H), 7.25-7.19 (m, 3 H), 3.84-3.75 (m, 1 H), 3.58 (dd, J=3.5, 13.1 Hz, 1 H), 3.13 (s, 2 H), 2.78 (dd, J=9.8, 13.1 Hz, 1 H), 2.43 (s, 3 H), 1.54-1.42 (m, 2 H), 0.99 (s, 3 H), 0.46 (s, 3 H); $^{13}$C NMR (100 MHz, CDCl$_3$) δ=143.3, 138.5, 135.3, 129.6, 129.5, 128.4, 127.6, 126.4, 61.7, 61.6, 45.7, 42.9, 37.2, 26.5, 25.8, 21.6; IR (thin film): 3061, 3027, 2960, 1288, 2873, 1599, 1540, 1494, 1245, 1454, 1390, 1347, 1303, 1224 cm$^{-1}$; LRMS (ESI): Calculated for [M+H$^+$]=344.48. found 344.12.

2-(4-Fluorobenzyl)-4,4-dimethyl-1-tosylpyrrolidine (2b)

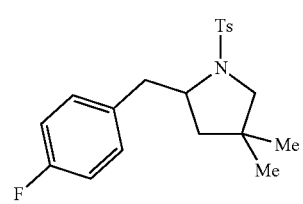 [SMILES: Cc1ccc(S(=O)(=O)N2CC(C)(C)CC2Cc2ccc(F)cc2)cc1]

Prepared using general procedure C on a 100 mg scale with 0.2 equiv thiophenol, and dichloroethane [0.5 M]. Irradiated for 24 h then purified in 2% EtOAc/Hexanes to give a white solid in 89% isolated yield (average of two trials). $^1$H NMR (400 MHz, CDCl$_3$) δ=7.75 (d, J=8.3 Hz, 2 H), 7.30 (d, J=8.5 Hz, 2 H), 7.20-7.13 (m, 2 H), 7.00-6.92 (m, 2 H), 3.78-3.69 (m, 1 H), 3.43 (dd, J=3.4, 13.4 Hz, 1 H), 3.07 (q, J=10.5 Hz, 2 H), 2.80 (dd, J=9.5, 13.3 Hz, 1 H), 2.40 (s, 3 H), 1.43 (d, J=8.0 Hz, 2 H), 0.94 (s, 3 H), 0.41 (s, 3 H); $^{13}$C NMR (100 MHz, CDCl$_3$) δ=143.4, 135.2, 134.0, 131.1, 131.0, 129.6, 127.5, 115.3, 115.1, 61.6, 61.4, 45.5, 41.7, 37.2, 26.4, 25.8, 21.6; IR (thin film): 2962, 1597, 1508, 1465, 1330, 1302, 1218 cm$^{-1}$; LRMS (ESI): Calculated for [M+H$^+$]=362.47. found 362.10.

2-(4-Methoxybenzyl)-4,4-dimethyl-1-tosylpyrrolidine (3b)

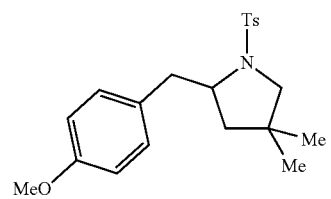 [SMILES: COc1ccc(CC2CC(C)(C)CN2S(=O)(=O)c2ccc(C)cc2)cc1]

Prepared using general procedure C on a 100 mg scale with 0.2 equiv thiophenol, and dichloroethane [0.5 M]. Irradiated for 30 h then purified in 5% EtOAc/Hexanes to give a colorless oil in 88% isolated yield (average of two trials). $^1$H NMR (400 MHz, CDCl$_3$) δ=7.76 (d, J=8.0 Hz, 2 H), 7.30 (d, J=8.3 Hz, 2 H), 7.12 (d, J=8.5 Hz, 2 H), 6.81 (d, J=8.5 Hz, 2 H), 3.87-3.76 (m, 3 H), 3.75-3.68 (m, 1 H), 3.45 (dd, J=3.4, 13.2 Hz, 1 H), 3.13-3.04 (m, 2 H), 2.72 (dd, J=9.7, 13.2 Hz, 1 H), 2.40 (s, 3 H), 1.52-1.42 (m, 2 H), 1.02-0.92 (m, 3 H), 0.42 (s, 3 H); $^{13}$C NMR (100 MHz, CDCl$_3$) δ=158.2, 143.3, 135.3, 130.5, 129.6, 127.5, 113.8, 61.7, 55.2, 45.7, 41.8, 37.2, 26.5, 25.8, 21.4; IR (thin film): 2958, 2872, 1683, 1612, 1582, 1511, 1464, 1390, 1346, 1302, 1247 cm$^{-1}$; LRMS (ESI): Calculated for [M+H$^+$]=374.51. found 374.15.

2-(2-Methoxybenzyl)-4,4-dimethyl-1-tosylpyrrolidine (4b)

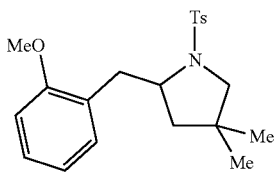 [SMILES: COc1ccccc1CC1CC(C)(C)CN1S(=O)(=O)c1ccc(C)cc1]

Prepared using general procedure C on a 100 mg scale with 0.2 equiv thiophenol, and dichloroethane [0.5 M]. Irradiated for 40 h then purified in 5% EtOAc/Hexanes to give a white solid in 69% isolated yield (average of two trials). $^1$H NMR (400 MHz, CDCl$_3$) δ=7.80 (d, J=8.3 Hz, 2 H), 7.30 (d, J=8.1 Hz, 2 H), 7.20-7.12 (m, 2 H), 6.89-6.80 (m, 2 H), 3.85 (s, 3 H), 3.83-3.76 (m, 1 H), 3.72 (dd, J=3.9, 12.7 Hz, 1 H), 3.22-3.16 (m, 1 H), 3.11-3.06 (m, 1 H), 2.68 (dd, J=10.3, 12.7 Hz, 1 H), 2.40 (s, 3 H), 1.48 (dd, J=8.2, 12.8 Hz, 1 H), 1.34 (dd, J=7.1, 12.7 Hz, 1 H), 0.99 (s, 3 H), 0.42 (s, 3 H); $^{13}$C NMR (100 MHz, CDCl$_3$) δ=157.7, 143.1, 135.0, 131.2, 129.4, 127.7, 127.7, 127.2, 120.5, 110.4, 62.1, 60.0, 55.3, 45.8, 37.5, 37.0, 26.7, 26.1, 21.6; IR (thin film) 2958, 2872, 1732, 1716, 1698, 1683, 1670, 1652, 1599, 1540, 1507, 1493, 1438, 1396, 1304, 1244 cm$^{-1}$; LRMS (ESI): Calculated for [M+H$^+$]=374.51. found 374.16.

2-(4-Methoxybenzyl)-1-tosylpyrrolidine (5b)

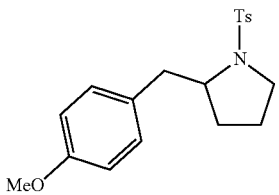 [SMILES: COc1ccc(CC2CCCN2S(=O)(=O)c2ccc(C)cc2)cc1]

Prepared using general procedure C on a 100 mg scale with 0.2 equiv thiophenol, and dichloroethane [0.5 M]. Irradiated for 48 h then purified in 5% EtOAc/Hexanes to give a colorless oil in 79% isolated yield (average of two trials). $^1$H NMR (400 MHz, CDCl$_3$) δ=7.73 (d, J=8.3 Hz, 2 H), 7.28 (d, J=8.0 Hz, 2 H), 7.16-7.10 (m, 2 H), 6.81 (d, J=8.5 Hz, 2 H), 3.77 (s, 3 H), 3.74 (d, J=3.8 Hz, 1 H), 3.39-3.31 (m, 1 H), 3.16-3.05 (m, 2 H), 2.69 (dd, J=9.4, 13.4 Hz, 1 H), 2.40 (s, 3 H), 1.65-1.54 (m, 2H), 1.47-1.34 (m, 2 H); $^{13}$C NMR (100 MHz, CDCl$_3$) δ=158.3, 143.3, 134.8, 130.6, 130.5, 129.7, 127.5, 113.8, 61.7, 55.3, 49.3, 41.7, 29.8, 23.8, 21.5; IR (thin film): 2953, 2835, 1612, 1597, 1583, 1511, 1399, 1339, 1247 cm$_{-1}$; LRMS (ESI): Calculated for [M+H$^+$]=346.46. found 346.12.

4-Isopropyl-2-(4-methoxybenzyl)-1-tosylpyrrolidine (6b)

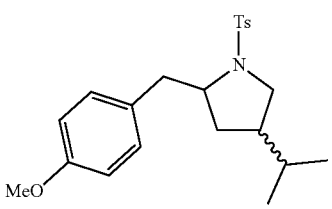 [SMILES: COc1ccc(CC2CC(C(C)C)CN2S(=O)(=O)c2ccc(C)cc2)cc1]

Prepared using general procedure C on a 100 mg scale with 0.2 equiv thiophenol, and dichloroethane [0.5 M]. Irradiated for 39 h then purified in 8% EtOAc/Hexanes to give a white solid in 88% isolated yield (average of two trials) in a 1.6:1 dr. $^1$H NMR (major) (400 MHz, CDCl$_3$) δ=7.73 (d, J=3.2, 8.1 Hz, 2 H), 7.33-7.27 (m, 2 H), 7.16-7.09 (m, 2 H), 6.85-6.78 (m, 2 H), 3.80 (d, J=2.7 Hz, 1 H), 3.76 (s, 3 H), 3.71-3.63 (m, 1 H), 3.62-3.51 (m, 1 H), 3.30 (dd, J=3.4, 13.4 Hz, 1 H), 2.85-2.71 (m, 1 H), 2.41 (s, 3 H), 1.79 (td, J=6.4, 12.8 Hz, 1 H), 1.27-1.10 (m, 2 H), 0.70 (t, J=7.3 Hz, 6 H) $^1$H NMR (minor) (400 MHz, CDCl$_3$) δ=7.74-7.70 (m, 2 H), 7.30 (d, J=5.1 Hz, 2 H), 7.14 (d, J=6.6 Hz, 2 H), 6.84-6.81 (m, 2 H), 3.76 (s, 3 H), 3.72-3.63 (m, 1 H), 3.62-3.51 (m, 1 H), 3.11 (dd, J=3.4, 13.4 Hz, 1 H), 2.69-2.54 (m, 1 H), 2.40 (s, 3 H), 1.73-1.65 (m, 1 H), 1.21-1.14 (m, 1 H), 1.03-0.90 (m, 2 H), 0.78 (d, J=6.6 Hz, 3 H), 0.74 (d, J=6.6 Hz, 3 H) $^{13}$C NMR (mix of isomers (100 MHz, CDCl$_3$) δ=158.2, 143.3, 135.3, 134.4, 130.7, 130.6, 130.5, 130.3, 129.7, 129.6, 127.5, 127.4, 113.9, 113.8, 62.5, 62.1, 55.3, 55.2, 53.4, 45.4, 44.1, 42.1, 41.9, 36.8, 34.0, 31.8, 31.2, 21.6, 21.5, 21.4, 21.3, 21.1, 21.0 IR (thin film): 3060, 3030, 2959, 2871, 2835, 1749, 1716, 1683, 1652, 1613, 1597, 1558, 1540, 1494, 1456, 1386, 1302, 1247 cm$^{-1}$; LRMS (ESI): Calculated for [M+H$^+$]=388.54. found 388.13.

4,4-Dimethyl-3-phenyl-1-tosylpiperidine (7b)

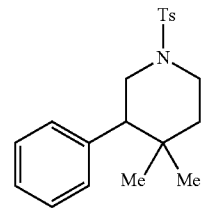 [SMILES: Cc1ccc(S(=O)(=O)N2CCC(C)(C)C(c3ccccc3)C2)cc1]

Prepared using general procedure C on a 100 mg scale with 0.2 equiv thiophenol, and dichloroethane [0.5 M]. Irradiated for 48 h then purified in 4% EtOAc/Hexanes to give a white solid in 79% isolated yield (average of two trials). $^1$H NMR (400 MHz, CDCl$_3$) δ=7.65 (d, J=8.3 Hz, 2 H), 7.33 (d, J=8.0 Hz, 2 H), 7.27-7.19 (m, 3 H), 7.01 (d, J=7.8 Hz, 2 H), 3.67 (d, J=12.0 Hz, 1 H), 3.61 (d, J=10.5 Hz, 1 H), 2.80-2.67 (m, 2 H), 2.58 (dt, J=2.8, 12.3 Hz, 1 H), 2.44 (s, 3 H), 1.71 (dt, J=4.5, 13.1 Hz, 1 H), 1.52-1.45 (m, 1 H), 0.79 (s, 3 H), 0.67 (s, 3 H); $^{13}$C NMR (100 MHz, CDCl$_3$) δ=143.5, 139.5, 133.6, 129.7, 129.1, 127.9, 126.9, 51.6, 46.4, 42.8, 39.7, 32.5, 29.9, 21.6, 19.3; IR (thin film): 2948, 1597, 1455, 1389, 1340, 1223 cm$^{-1}$; LRMS (ESI): Calculated for [M+H$^+$]=344.48. found 344.06.

3-Phenyl-1-tosylpiperidine (8b)

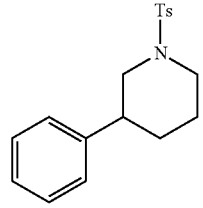 [SMILES: Cc1ccc(S(=O)(=O)N2CCCC(c3ccccc3)C2)cc1]

Prepared using general procedure C on a 100 mg scale with 0.2 equiv thiophenol, and dichloroethane [0.5 M]. Irradiated for 96 h then purified in 5% EtOAc/Hexanes to give a colorless oil in 60% isolated yield (average of two trials). Spectral data were in agreement with literature values.[10] (Verendel, J. J. et al., *J. Am. Chem. Soc.* 2010, 132, 8880-8881). $^1$H NMR (400 MHz, CDCl$_3$) δ=7.62 (d, J=8.3 Hz, 2 H), 7.33-7.26 (m, 4 H), 7.25-7.19 (m, 1 H), 7.16 (d, J=7.0 Hz, 2 H), 3.91-3.81 (m, 2 H), 2.92-2.81 (m, 1 H), 2.42 (s, 3 H), 2.32-2.17 (m, 2 H), 1.93 (d, J=13.3 Hz, 1 H), 1.87-1.70 (m, 2 H), 1.48-1.35 (m, 1 H).

2-Isopropyl-4,4-diphenyl-1-tosylpyrrolidine (9b)

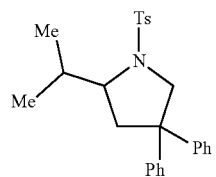

Prepared using general procedure C on a 100 mg scale with 0.2 equiv thiophenol, and dichloroethane [0.5 M]. Irradiated for 96 h then purified in 3% EtOAc/Hexanes to give a colorless oil in 70% isolated yield (average of two trials). $^1$H NMR (400 MHz, CDCl$_3$) δ=7.42 (d, J=8.3 Hz, 2 H), 7.22 (d, J=7.8 Hz, 2 H), 7.15 (d, J=7.3 Hz, 1 H), 7.10 (dd, J=1.9, 10.2 Hz, 4 H), 7.06-7.00 (m, 5 H), 4.47 (dd, J=1.8, 11.0 Hz, 1 H), 3.91 (d, J=11.0 Hz, 1 H), 3.74 (s, 1 H), 2.75-2.67 (m, 1 H), 2.57-2.47 (m, 1 H), 2.33 (s, 3 H), 2.23 (dd, J=10.4, 12.9 Hz, 1 H), 0.88 (d, J=7.0 Hz, 3 H), 0.74 (d, J=6.8 Hz, 3 H); $^{13}$C NMR (100 MHz, CDCl$_3$) δ=146.3, 144.3, 142.5, 136.7, 129.3, 128.6, 128.5, 126.7, 126.7, 126.5, 126.5, 126.1, 64.5, 59.9, 52.4, 36.9, 30.0, 21.5, 19.4, 14.7; IR (thin film): 3058, 2962, 1598, 1495, 1447, 1389, 1336, 1304, 1265, 1235 cm$^{-1}$; LRMS (ESI): Calculated for [M+H$^+$]=420.58. found 420.15.

(2S,5S)-2-Isopropyl-5-methyl-1-tosylpyrrolidine (10b)

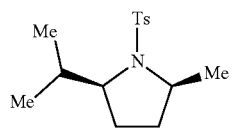 [SMILES: Cc1ccc(S(=O)(=O)N2[C@@H](C)CC[C@H]2C(C)C)cc1]

Prepared using general procedure C on a 100 mg scale with 0.2 equiv thiophenol, and dichloroethane [0.5 M]. Irradiated for 96 h then purified in 3% EtOAc/Hexanes to give a colorless oil in 56% isolated yield (average of two trials) in 3:1 dr. Spectral data were in agreement with literature values.[11] (Sherman, E. S. et al., *J. Org. Chem.* 2007, 72, 3896-3905). $^1$H NMR (major) (400 MHz, CDCl$_3$) δ=7.71-7.67 (m, 2 H), 7.27 (d, J=7.8 Hz, 2 H), 3.71-3.63 (m, 1 H), 3.43-3.36 (m, 1 H), 2.40 (s, 3 H), 2.11-2.00 (m, 1 H), 1.62 (td, J=6.1, 12.1 Hz, 1 H), 1.56-1.45 (m, 1 H), 1.44-1.34 (m, 1 H), 1.31-1.23 (m, 4 H), 0.96 (d, J=7.0 Hz, 3 H), 0.90 (d, J=6.8 Hz, 3 H).

1-Tosyloctahydro-1H-indole (11b)

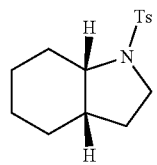 [SMILES: Cc1ccc(S(=O)(=O)N2CC[C@@H]3CCCC[C@@H]32)cc1]

Prepared using general procedure C on a 100 mg scale with 0.2 equiv thiophenol, and dichloroethane [0.5 M]. Irradiated for 96 h then purified in 5% EtOAc/Hexanes to give a colorless oil in 72% isolated yield (average of two trials) in 12:1 dr. Spectral data were in agreement with literature values.[12] (Klein, J. E. M. N. et al., *Org. Biomol. Chem.* 2009, 7, 986-995). $^1$H NMR major (400 MHz, CDCl$_3$) δ=7.72-7.65 (m, 2 H), 7.29-7.22 (m, 2 H), 3.56-3.42 (m, 2 H), 3.19-3.09 (m, 1 H), 2.42-2.35 (m, 3 H), 1.91-1.69 (m, 3 H), 1.63-1.46 (m, 5 H), 1.39-1.23 (m, 2 H), 1.23-1.11 (m, 1 H).

4-Benzyl-1,2,3-oxathiazinane 2,2-dioxide (12b)

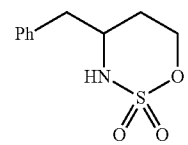

Prepared using general procedure C on a 100 mg scale with 0.2 equiv thiophenol, and dichloroethane [0.5 M]. Irradiated for 96 h then purified in 20% EtOAc/Hexanes to give an off-white solid 54% isolated yield (average of two trials). $^1$H NMR (400 MHz, CDCl$_3$) δ=7.36-7.29 (m, 2 H), 7.28-7.24 (m, 1 H), 7.18-7.14 (m, 2 H), 4.66 (dt, J=2.8, 12.0 Hz, 1 H), 4.48 (ddd, J=1.8, 4.9, 11.6 Hz, 1 H), 4.10 (d, J=10.0 Hz, 1 H), 4.03-3.90 (m, 1 H), 2.92 (dd, J=5.9, 13.7 Hz, 1 H), 2.77 (dd, J=7.3, 13.7 Hz, 1 H), 1.81-1.62 (m, 2 H) $^{13}$C NMR (100 MHz, CDCl$_3$) δ=135.4, 129.4, 129.0, 127.4, 72.0, 56.5, 41.1, 29.0 3 IR (thin film): 3259, 3086, 3062, 2965, 2925, 2855, 1698, 1683, 1670, 1636, 1602, 1558, 1523, 1497, 1455, 1420, 1360, 1267, 1239, 1220 cm$^{-1}$; LRMS (ESI): Calculated for [M+H$^+$]=227.28. found 227.99.

Procedure for Control Reactions:

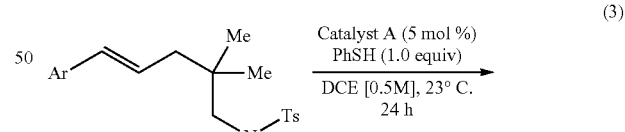

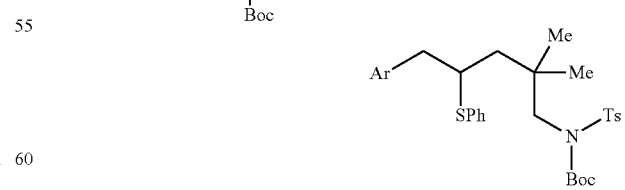

Ar = p-(F)C$_6$H$_4$

Not Observed

Equation 3: To a clean flame-dried 1 dram vial was added a magnetic stir bar, N-Me-mesityl acridinium catalyst (5.0 mol %), (E)-tert-butyl (5-(4-fluorophenyl)-2,2-dimethyl-pent-4-en-1-yl)(tosyl)carbamate (100 mg). Reaction vessel was purged with nitrogen then dichloroethane (sparged for 15 min, [0.5M]) was added then thiophenol was added (1.0 equiv). Reaction was sealed with teflon tape then irradiated with blue LED lamp at room temperature for 24 hours. Reaction was quenched with a solution of TEMPO (~5 mg) in dichloromethane (0.2 mL) and concentrated in vacuo. Only unchanged starting material was observed by $^1$H NMR.

(4)

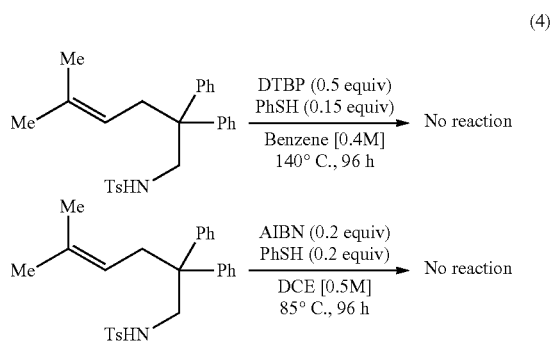

Equation 4, Conditions A: To a clean dry 20 mL scintillation vial was added a magnetic stir bar, 4-Methyl-N-(5-methyl-2,2-diphenylhex-4-en-1-yl)benzenesulfonamide (1 equiv), benzene [0.4 M], ditert-butyl peroxide (0.5 equiv) and thiophenol (0.15 equiv) under nitrogen. Reaction vessel was sealed and heated to 140° C. for 96 hours, then heating was discontinued and reaction mixture was quenched with TEMPO solution, and concentrated in vacuo. Only unchanged starting material was observed by $^1$H NMR.

Equation 4, Conditions B: To a clean dry 20 mL scintillation vial was added a magnetic stir bar, 4-Methyl-N-(5-methyl-2,2-diphenylhex-4-en-1-yl)benzenesulfonamide (1 equiv), dichloroethane[0.5 M], azobisisobutyronitrile (0.2 equiv) and thiophenol (0.2 equiv) under nitrogen. Reaction vessel was sealed and heated to 85° C. for 96 hours, then heating was discontinued and reaction mixture was quenched with TEMPO solution, and concentrated in vacuo. Only unchanged starting material was observed by $^1$H NMR.

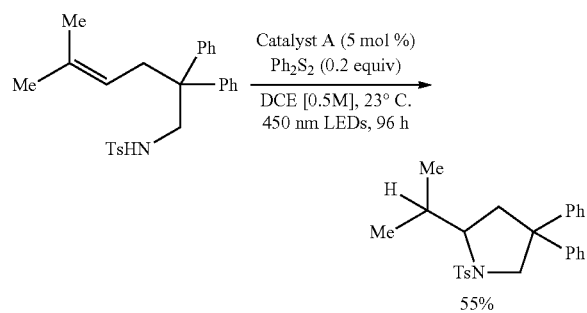

To a clean flame-dried 1 dram vial was added a magnetic stir bar, N-Me-mesityl acridinium catalyst (5.0 mol %), 4-Methyl-N-(5-methyl-2,2-diphenylhex-4-en-1-yl)benzenesulfonamide (100 mg) and diphenyldisulfide (0.2 equiv). Reaction vessel was purged with nitrogen then dichloroethane (sparged for 15 min, [0.5M]) was added. Reaction was sealed with teflon tape then irradiated with blue LED lamp at room temperature for 96 hours. Reaction was quenched with a solution of TEMPO (~5 mg) in dichloromethane (0.2 mL) and concentrated in vacuo. Crude $^1$H NMR with hexamethyldisiloxane indicated a 55% yield of desired product.

REFERENCES (1) Müller, T. E.; Hultzsch, K. C.; Yus, M.; Foubelo, F.; Tada, M. *Chem. Rev.* 2008, 108, 3795.

(2) O'Hagan, D. *Nat. Prod. Rep.* 2000, 17, 435.

(3) For selected examples of intramolecular Markovnikov hydroaminations catalyzed by complexes of group IV metals and lanthanides, see: (a) Manna, K.; Xu, S.; Sadow, A. D. *Angew. Chem., Int. Ed.* 2011, 50, 1865. (b) Leitch, D. C.; Payne, P. R.; Dunbar, C. R.; Schafer, L. L. *J. Am, Chem. Soc.* 2009, 131, 18246. (c) Wood, M. C.; Leitch, D. C.; Yeung, C. S.; Kozak, J. A.; Schafer, L. L. *Angew. Chem., Int. Ed.* 2007, 46, 354. (d) Watson, D. A.; Chiu, M.; Bergman, R. G. *Organometallics* 2006, 25, 4731. (e) Gribkov, D. V.; Hultzsch, K. C.; Hampel, F. *J. Am. Chem. Soc.* 2006, 128, 3748. (f) Kim, J. Y.; Livinghouse, T. *Org. Lett.* 2005, 7, 1737. (g) Hong, S.; Marks, T. J. *Acc. Chem. Res.* 2004, 37, 673. (h) Hong, S.; Tian, S.; Metz, M. V.; Marks, T. J. *J. Am. Chem. Soc.* 2003, 125, 14768.

(4) For selected examples of intramolecular Markovnikov hydroaminations catalyzed by late transition metals and lanthanides, see: (a) Chapurina, Y.; Ibrahim, H.; Guillot, R.; Kolodziej, E.; Collin, J.; Trifonov, A.; Schultz, E.; Hannedouche, J. *J. Org. Chem.* 2011, 76, 10163. (b) Shen, X.; Buchwald, S. L. *Angew. Chem., Int. Ed.* 2010, 49, 564. (c) Julian, L. D.; Hartwig, J. F. *J. Am. Chem. Soc.* 2010, 132, 13813. (d) Ohmiya, H.; Moriya, T.; Sawamura, M. *Org. Lett.* 2009, 11, 2145. (e) Hesp, K. D.; Tobisch, S.; Stradiotto, M. *J. Am. Chem. Soc.* 2009, 132, 413. (f) Liu, Z.; Hartwig, J. F. *J. Am. Chem. Soc.* 2008, 130, 1570. (g) Cochran, B. M.; Michael, F. E. *J. Am. Chem. Soc.* 2008, 130, 2786. (o) Michael, F. E.; Cochran, B. M. *J. Am. Chem. Soc.* 2006, 128, 4246. (h) Han, X.; Widenhoefer, R. A. *Angew. Chem., Int. Ed.* 2006, 45, 1747. (i) Bender, C. F.; Widenhoefer, R. A. *J. Am. Chem. Soc.* 2005, 127, 1070. For selected examples of intermolecular Markovnikov hydroaminations, see: (j) Zhou, J.; Hartwig, J. F. *J. Am. Chem. Soc.* 2008, 130, 12220. (k) McBee, J. L.; Bell, A. T.; Tilley, T. D. *J. Am. Chem. Soc.* 2008, 130, 16562. (l) Brunet, J.-J.; Chu, N.-C.; Rodriguez-Zubiri, M. *Eur. J. Inorg. Chem.* 2007, 4711. (m) Zhang, J.; Yang, C.-G.; He, C. *J. Am. Chem. Soc.* 2006, 128, 1798. (n) Rosenfeld, D. C.; Shekhar, S.; Takemiya, A.; Utsunomiya, M.; Hartwig, J. F. *Org. Lett.* 2006, 8, 4179. (o) Dorta, R.; Egli, P.; Zürcher, F.; Togni, A. *J. Am. Chem. Soc.* 1997, 119, 10857. (p) Casalnuovo, A. L.; Calabrese, J. C.; Milstein, D. *J. Am. Chem. Soc.* 1988, 110, 6738.

(5) For selected examples of intermolecular anti-Markovnikov hydroaminations, see: (a) Utsunomiya, M.; Kuwano, R.; Kawatsura, M.; Hartwig, J. F. *J. Am. Chem. Soc.* 2003, 125, 5608. (b) Munro-Leighton, C.; Blue, E. D.; Gunnoe, T. B. *J. Am. Chem. Soc.* 2006, 128, 1446, (c) Fadini, L.; Togni, A. *Chem. Commun.* 2003, 30. (d) Seligson, A. L.; Trogler, W. C. *Organometallics* 1993, 12, 744. (e) Castonguay, A.; Spasyuk, D. M.; Madern, N.; Beauchamp, A. L.; Zargarian, D. *Organometallics* 2009, 28, 2134. (f) Kawatsura, M.; Hartwig, J. F. *Organometallics* 2001, 20, 1960. (g) Beller, M.; Trauthwein, H.; Eichberger, M.; Breindl, C.; Herwig, J.; Müller, T. E.; Thiel, O. R. *Chem. Eur J.* 1999, 5, 1306. (h) Ryu, J.-S.; Li, G. Y.; Marks, T. J. *J. Am. Chem. Soc.* 2003, 125, 12584. (i) Utsunomiya, M.; Hartwig, J. F. *J. Am.*

*Chem. Soc.* 2004, 126, 2702. (j) Takaya, J.; Hartwig, J. F. *J. Am. Chem. Soc.* 2005, 127, 5756. (k) Munro-Leighton, C.; Delp, S. A.; Alsop, N. M.; Blue, E. D.; Gunnoe, T. B. *Chem. Commun.* 2008, 1, 111. (1) Brinkmann, C.; Barrett, A. G. M.; Hill, M. S.; Procopiou, P. A. *J. Am. Chem. Soc.* 2012, 134, 2193.

(6) Yasuda, M.; Yamashita, T.; Shima, K.; Pac, C. *J. Org. Chem.* 1987, 52, 753.

(7) For a recent example of a formal intermolecular anti-Markovnikov alkene hydroamination, see: Rucker, R.; Whittaker, A. M.; Dang, H.; Lalic, G. *J. Am. Chem. Soc.* 2012, 134, 6571.

(8) Takemiya, A.; Hartwig, J. F. *J. Am. Chem. Soc.* 2006, 128, 6042.

(9) For examples of formal intramolecular anti-Markovnikov alkene hydroaminations, see: (a) Pronin, S. V.; Tabor, M. G.; Jansen, D. J.; Shenvi, R. A. *J. Am. Chem. Soc.* 2012, 134, 2012. (b) Shirai, M.; Brebion, F.; Rumthao, S.; Crich, D. *Tetrahedron* 2006, 62, 6501.

(10) Hamilton, D. S.; Nicewicz, D. A. *J. Am. Chem. Soc.* 2012, 134, 18577.

(11) Arnold, D. R.; Chan, M. S. W.; McManus, K. A. *Can. J. Chem.* 1996, 74, 2143.

(12) Gassman, P. G.; Bottorff, K. J. *J. Am. Chem. Soc.* 1987, 109, 7547.

(13) Mangion, D.; Arnold, D. R. *Acc. Chem. Res.* 2002, 35, 297.

(14) For reactions of amines with electrochemically-generated alkene cation radicals, see: (a) Ashikari, Y.; Nokami, T.; Yoshida, J. *J. Am. Chem. Soc.* 2011, 133, 11840. (b) Campbell, J. M.; Xu, H.; Moeller, K. D. *J. Am. Chem. Soc.* 2012, 134, 18338. (c) Xu, H.; Moeller, K. D. *Org. Lett.* 2010, 12, 5174. (d) Xu, H.; Moeller, K. D. *J. Am. Chem. Soc.* 2010, 132, 2839. (e) Xu, H.; Moeller, K. D. *J. Am. Chem. Soc.* 2008, 130, 13542.

(15) (a) Furst, L.; Matsuura, B. S.; Narayanam, J. M. R.; Tucker, J. W.; Stephenson, C. R. J. *Org. Lett.* 2010, 12, 3104. (b) Condie, A. G.; González-Gómez, J. C.; Stephenson C. R. J. *J. Am. Chem. Soc.* 2010, 132, 1464. (c) Dai, C.; Meschini, F.; Narayanam, J. M. R.; Stephenson, C. R. J. *J. Org. Chem.* 2012, 77, 4425. (d) Zhu, S.; Das, A.; Bui, L.; Zhou, H.; Curran, D. P.; Rueping, M. *J. Am. Chem. Soc.* 2013, 135, 1823. (e) Hari, D. P.; König, B. *Org. Lett.* 2011, 13, 3852. (f) Fu, W.; Guo, W.; Zou, G.; Xu C. *J. Fluorine Chem.* 2012, 140, 88.

(16) For lead references, see: (a) Tokuda, M. et al., Tetrahedron 1991, 47, 747. (b) Tokuda, M. et al., *Tetrahedron* 1993, 49, 2413. For an excellent recent enantioselective example, see: (c) Zhang, X. et al., *Angew. Chem. Int. Ed.* 2012, 51, 394.

(17) Tyson, E. L.; Ament, M. S.; Yoon, T. P. *J. Org. Chem.* 2013, 78, 2046.

(18) Roberts, B. P. *Chem. Soc. Rev.* 1999, 28, 25.

(19) Toteberg-Kaulen, S.; Steekhan, E. *Tetrahedron* 1988, 44, 4389.

(20) Armstrong, D. A.; Sun, Q.; Schuler, R. H. *J. Phys. Chem.* 1996, 100, 9892.

(21) Ohkubo, K. et al., *Chem. Commun.* 2010, 46, 601.

The foregoing is illustrative of the present invention, and is not to be construed as limiting thereof. The invention is defined by the following claims, with equivalents of the claims to be included therein.

That which is claimed is:

1. A method of making an anti-Markovnikov addition product, comprising:
reacting an acid with an Acne or alkyne in a dual catalyst reaction system to the exclusion of oxygen to produce said anti-Markovnikov addition product;
said dual catalyst reaction system comprising a single electron oxidation catalyst in combination with a hydrogen atom donor catalyst, wherein said single electron oxidation catalyst is a ground state oxidation catalyst;
wherein said hydrogen atom donor catalyst is a compound of the Formula A-SH, where A is alkyl, aryl, or an electron withdrawing group.

2. The method of claim 1, wherein said anti-Markovnikov addition product is produced regioselectively in a ratio of at least 5:1 of anti-Markovnikov addition product to Markovnikov addition product.

3. The method of claim 1, wherein A is selected from the group consisting of alkyl, aryl, carboxyl, and carbonyl groups.

4. The method of claim 1, wherein said single electron oxidation catalyst is a photocatalyst.

5. The method of claim 4, wherein said photocatalyst comprises a carbocyclic or heterocyclic aromatic compound containing ring nitrogen heteroatoms.

6. The method of claim 5, wherein said photocatalyst comprises an anthracene, aza-anthracene or polyaza-anthracene nucleus which is unsubstituted, substituted or polysubstituted at any position with halogen, and/or with one or more lower alkyl or cycloalkyl radicals, and/or with other phenyl substituents.

7. The method of claim 4, wherein said photocatalyst has a reduction potential of about −1.0 V to +0.1 V against a saturated calomel reference electrode in 100 percent acetonitrile as determined by cyclic voltammetry.

8. The method of claim 1, wherein said ground state oxidation catalyst is selected from the group consisting of eerie ammonium nitrate, ferrocenium tetrafluoroberate, nitrosyl tetrafluoroborate, iron trichloride, iron (III) tris (phenanthroline) tris(hexafluorophosphate), and tris(4-bromopheny)aminium hexafluoroantimonate.

9. The method of claim , wherein said reaction system is free of transition metal catalysts.

10. The method of claim 1, wherein said reacting is an intramolecular hydroalkoxylation reaction.

11. The method of claim 1, wherein said reacting is an intramolecular hydrolactonization reaction.

12. The method of claim 1, wherein said reacting is an intermolecular hydroacetoxylation reaction.

13. The method of claim 1, wherein said reacting is an anti-Markovnikov polymerization reaction where the acid and alkene group are contained within the same monomeric unit or are contained on separate monomeric units.

* * * * *

UNITED STATES PATENT AND TRADEMARK OFFICE
CERTIFICATE OF CORRECTION

PATENT NO. : 10,017,441 B2
APPLICATION NO. : 14/787179
DATED : July 10, 2018
INVENTOR(S) : Nicewicz et al.

It is certified that error appears in the above-identified patent and that said Letters Patent is hereby corrected as shown below:

In the Specification

Column 21, Line 11: delete "ER" and insert -- ESI --

Column 23, Line 66: delete "EST" and insert -- ESI --

In the Claims

Column 36, Claim 1, Line 8: delete "Acne" and insert -- alkene --

Column 36, Claim 8, Line 42: delete "eerie" and insert -- ceric --

Column 36, Claim 8, Line 45: delete "mopheny" and insert -- mophenyl --

Column 36, Claim 9, Line 46: delete "claim ," and insert -- claim 1, --

Signed and Sealed this
Sixth Day of November, 2018

Andrei Iancu
*Director of the United States Patent and Trademark Office*